(12) United States Patent  (10) Patent No.: US 9,961,969 B2
Kawabata et al.  (45) Date of Patent: May 8, 2018

(54) BELT AND WEARABLE DEVICE

(71) Applicant: OMRON HEALTHCARE Co., Ltd., Kyoto (JP)

(72) Inventors: Yasuhiro Kawabata, Kyoto (JP); Tatsuya Kobayashi, Kyoto (JP); Reiji Fujita, Kyoto (JP); Hiroshi Nakamori, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 23 days.

(21) Appl. No.: 15/365,348

(22) Filed: Nov. 30, 2016

(65) Prior Publication Data

US 2017/0360162 A1 Dec. 21, 2017

Related U.S. Application Data

(63) Continuation of application No. PCT/JP2015/063983, filed on May 15, 2015.

(30) Foreign Application Priority Data

May 30, 2014 (JP) .................................. 2014-113329

(51) Int. Cl.
A44C 5/20 (2006.01)
A44C 5/00 (2006.01)
(Continued)

(52) U.S. Cl.
CPC .............. A44C 5/0069 (2013.01); A44C 5/20 (2013.01); A45F 5/00 (2013.01); A61B 5/02438 (2013.01);
(Continued)

(58) Field of Classification Search
CPC . A44C 5/0069; A44C 5/20; A45F 5/00; A45F 2005/008; A61B 5/02438;
(Continued)

(56) References Cited

U.S. PATENT DOCUMENTS 316,872 A * 4/1885 Bretzfield ............ A44B 11/006
24/164
3,109,212 A * 11/1963 Emery ................... B65D 63/14
24/16 PB
(Continued)

FOREIGN PATENT DOCUMENTS

CH 208598 A 2/1940
GB 289750 A 5/1928
(Continued)

OTHER PUBLICATIONS

International Search Report issued in PCT Application No. PCT/JP2015/063983, dated Jul. 28, 2015 (2 pages).
(Continued)

Primary Examiner — Corey Skurdal
(74) Attorney, Agent, or Firm — Osha Liang LLP

(57) ABSTRACT

A belt includes a belt main body extending in a long, narrow band. A frame-shaped body is attached to a first belt portion corresponding to a side on an end in a lengthwise direction of the belt main body. Multiple through-holes are formed in alignment in the lengthwise direction in a second belt portion corresponding to a side opposite to the first belt portion in the lengthwise direction of the belt main body. A locking member is included for attachment to a through-hole of the second belt portion so as to protrude from a front surface of the second belt portion. When the belt main body is mounted on the target object, the second belt portion is passed through the frame-shaped body, and the side of the frame-shaped body locks the locking member so as to prevent the second belt portion from coming out of the frame-shaped body.

14 Claims, 26 Drawing Sheets

(51) Int. Cl.
*A45F 5/00* (2006.01)
*A61B 5/024* (2006.01)
*A61B 5/11* (2006.01)
*A61B 5/00* (2006.01)

(52) U.S. Cl.
CPC .......... *A61B 5/1118* (2013.01); *A61B 5/6831* (2013.01); *A45F 2005/008* (2013.01)

(58) Field of Classification Search
CPC . A61B 5/1118; A61B 5/6831; Y10T 24/4782; Y10T 24/42
See application file for complete search history.

(56) References Cited

U.S. PATENT DOCUMENTS

| | | | | |
|---|---|---|---|---|
| 3,155,987 | A | 11/1964 | McGill et al. | |
| 3,929,265 | A * | 12/1975 | Pyne | A44C 5/16 224/178 |
| 4,221,063 | A * | 9/1980 | Charles | G09F 3/005 283/75 |
| 5,226,809 | A * | 7/1993 | Franco | A44B 17/0029 24/662 |
| 5,732,448 | A * | 3/1998 | Shields | A44B 11/22 24/170 |
| 6,343,384 | B1 * | 2/2002 | Ida | A41F 1/008 2/236 |
| 7,872,588 | B2 * | 1/2011 | Potter | G08B 21/0286 2/338 |
| 8,522,405 | B2 * | 9/2013 | Spielberger | A44B 11/20 2/311 |
| 9,314,072 | B2 * | 4/2016 | Lee | A44B 11/24 |
| 2009/0265971 | A1 * | 10/2009 | Cook | G09F 3/005 40/633 |
| 2010/0331145 | A1 * | 12/2010 | Lakovic | G04F 10/00 482/8 |
| 2015/0265034 | A1 * | 9/2015 | Lee | A45F 5/00 224/219 |

FOREIGN PATENT DOCUMENTS

| | | |
|---|---|---|
| JP | S36-009427 Y | 4/1961 |
| JP | S50-39175 Y | 11/1975 |
| JP | S57-124208 U | 8/1982 |
| JP | S58-44910 U1 | 3/1983 |
| JP | S58-168307 U | 11/1983 |
| JP | S60-91016 U | 6/1985 |

OTHER PUBLICATIONS

Written Opinion issued in PCT Application No. PCT/JP2015/063983, dated Jul. 28, 2015 (4 pages).
Softbank Mobile Corporation, "Healthcare (health device) activity level meter (wristband)", [online], on sale Jul. 18, 2013, [searched for on Mar. 14, 2014], www.softbank.jp/mobile/product/healthcare/ (2 pages).

* cited by examiner

BELT AND WEARABLE DEVICE

FIELD OF THE INVENTION

The present invention relates to a belt, and more specifically relates to a belt that is mounted by being wrapped around a substantially rod-shaped target object.

Also, the invention relates to a wearable device including such a belt and a device body that is to be mounted on a body using the belt.

DESCRIPTION OF RELATED ART

Conventionally, as disclosed in Non-Patent Literature 1 (Softbank Mobile Corporate, "Healthcare (health device) activity level meter (wristband)", [online], on sale Jul. 18, 2013, [searched for on Mar. 14, 2014], www.softbank.jp/mobile/product/healthcare/), for example, a wristband that is mounted by being wrapped around a wrist is known as this type of belt (also referred to as a "band"). This wristband includes a belt main body that extends in a long, narrow shape, and an activity level meter is installed in approximately the center of the belt main body. A protrusion is attached in a fixed manner near one end of the belt main body in an orientation of facing inward (toward the wrist) when mounted. Multiple through-holes into which the protrusion can be fitted are formed in alignment in the lengthwise direction of the belt main body in the vicinity of the other end of the belt main body.

CITATION LIST

Non-Patent Literature

Non-Patent Literature 1: Softbank Mobile Corporation, "Healthcare (health device) activity level meter (wristband)", [online], on sale Jul. 18, 2013, [searched for on Mar. 14, 2014], www.softbank.jp/mobile/product/healthcare/

SUMMARY OF INVENTION

When the above-described wristband is to be mounted on a wrist, for example, the belt main body is brought to the wrist such that the one end is on the outer side and the other is on the inner side, and the protrusion is fit into the corresponding through-hole by being inserted therein facing inward. Accordingly, the above-described wristband is mounted on the wrist.

However, with the above-described wristband, when the belt main body is to be mounted on the wrist, there is a possibility that a different through-hole among the multiple through-holes will be selected depending on the force applied to the belt main body, and the belt main body will be wrapped tightly or loosely each time mounting is performed. For this reason, the tensile force of the belt main body in the mounted state varies. As a result, with the above-described wristband, there is a risk that the activity level measurement accuracy will be impaired.

In view of this, one or more embodiments of the claimed invention provide a belt that is to be mounted by being wrapped around a substantially rod-shaped target object, and according to which the tensile force of a belt main body in a state of being mounted on the target object can be set appropriately.

Also, one or more embodiments of the claimed invention provide a wearable device that includes such a belt and a device main body, and is configured such that the device main body can be mounted on a body using the belt.

A belt according to one or more embodiments of the claimed invention is a belt to be mounted by being wrapped around a substantially rod-shaped target object, including: a belt main body that is flexible and extends in the form of a long, narrow band; a frame-shaped body attached to a first belt portion that corresponds to a side on an end in a lengthwise direction of the belt main body; a plurality of through-holes formed in alignment in the lengthwise direction in a second belt portion corresponding to a side opposite to the first belt portion in the lengthwise direction of the belt main body; and a locking member configured separately from the belt main body, the locking member being attached to the second belt portion in a mode in which only a head portion of the locking member protrudes from a front surface of the second belt portion due to the head portion being pushed through a through hole from a rear surface side of the second belt portion in advance, before the belt is mounted on the target object, wherein the locking member includes a flat base portion to be arranged in contact with the rear surface of the second belt, a neck portion that is continuous with the base portion and is to extend through the through hole to the front surface of the second belt portion, and the head portion that is provided on a leading end of the neck portion and has a dimension greater than a dimension of the through hole, and the locking member is formed integrally, and in a state in which the belt main body is mounted on a target object, the second belt portion is passed through the frame-shaped body, and a side of the frame-shaped body locks the head portion of the locking member so as to prevent the second belt portion from coming out of the frame-shaped body.

The present specification encompasses the case where the "target object" is a site such as a wrist, arm, torso, or leg, and the case where the "target object" is a structure other than a body, and the like.

Also, the "belt main body" may be provided with a device such as an activity level meter or a pulse meter between the first belt portion and the second belt portion, for example. If the belt main body is provided with a device, the first belt portion and the second belt portion of the belt main body may be formed separately and coupled via the device.

Also, the target object being "substantially rod-shaped" means that the cross-sectional shape of the target object may be circular, elliptical, oval-shaped, polygonal, or the like. Also, this means that the cross-sectional dimensions of the target object may change in various ways, such as becoming larger or smaller, according to the position in the lengthwise direction.

Also, the "rear surface" of the second belt portion refers to a surface on the inner circumferential side in a state in which the belt main body is mounted on the target object. The "front surface" of the second belt portion indicates a surface on the outer circumferential side in a state in which the belt main body is mounted on the target object.

Also, the "frame-shaped body" need only be substantially frame-shaped, and the shape of the frame may be rectangular, circular, elliptical, oval-shaped, polygonal, or the like. Also, the "frame-shaped body" may be formed by forming a portion to be directly attached to (to come into contact with) the first belt portion and the remaining portions as separate components and combining these multiple components, for example.

The "side" of the above-described frame-shaped body that locks the locking member indicates a side corresponding to the side opposite to the portion that is to be directly attached to (come into contact with) the above-described first belt portion.

The belt according to one or more embodiments of the claimed invention includes a locking member that is configured separately from the belt main body. The locking member is formed integrally. When mounting the belt according to one or more embodiments of the claimed invention on the target object, the user attaches the locking member to the second belt portion in a mode in which only the head portion protrudes from the front surface of the second belt portion by pushing the head portion of the locking member through a specific through-hole among the multiple through-holes formed in the second belt portion of the belt main body from the rear surface side of the second belt portion in advance. Accordingly, the locking member is easily attached to the through-hole. The mode of attaching the locking member is a mode in which a flat, planar base portion comes into contact with the rear surface of the second belt portion, the neck portion, which is continuous with the base portion, extends through the through-hole to the front surface of the second belt portion, and the head portion protrudes outward from the front surface. Because the head portion of the locking member has a dimension that is greater than a dimension of the through-hole, the locking member does not detach naturally once the locking member is attached to the through-hole.

When actually mounting the belt on the target object, the user first passes the leading end of the second belt portion through the frame-shaped body attached to the first belt portion such that the belt main body is wrapped around the target object. Next, the user pulls the leading end of the second belt portion until the head portion of the locking member goes past the side of the frame-shaped body, and the user releases the leading end. Upon doing so, the side of the frame-shaped body locks the head portion of the locking member, which prevents the second belt portion from coming out of the frame-shaped body. In this manner, the belt is mounted on the target object.

Thus, with the belt according to one or more embodiments of the claimed invention, before being mounted on the target object, the locking member is attached in advance to the specific through-hole of the second belt portion of the belt main body. Accordingly, in the state in which the belt main body is mounted on the target member, the length in the circumferential direction from the side of the frame-shaped body to the head portion of the locking member is stable, and the tensile force of the belt main body is set appropriately. As a result, when a device including the function of an activity level meter, a pulse meter, or the like is installed in the belt main body, for example, the device performs measurement stably.

As the specific through-hole, it is desirable to select a through-hole that overlaps with the side of the frame-shaped body when the belt main body is wrapped around the target object with a certain tensile force (includes the case where the tensile force is substantially zero as well), for example. Accordingly, in the state in which the belt main body is mounted on the target object, the belt main body is wrapped around the target object with that tensile force.

It is desirable that the multiple through-holes formed in the second belt portion have the same shape as each other. In this case, it is possible to use (attach) the same locking member for the multiple through-holes.

Note that at each position in the lengthwise direction of the second belt portion, one through-hole may be formed, or a set (referred to as a "through-hole set" as appropriate) of multiple (e.g., two) through-holes may be formed. If a set of multiple through-holes is formed at each position in the lengthwise direction of the second belt portion, the locking member includes, on a shared base portion, multiple neck portions corresponding to the through-hole sets and head portions provided on the leading ends of the respective neck portions.

In the state in which the belt main body is mounted on the target object, the side of the frame-shaped member locks the head portion of the locking member. Here, from the side of the frame-shaped body, the head portion of the locking member receives the force toward the leading end of the second belt portion in the lengthwise direction. The force is received due to the neck portion of the locking member being supported by the through-hole and the base portion being supported by the rear surface of the second belt portion. Accordingly, the locking member does not detach due to the force received from the side of the frame-shaped body.

With the belt according to an embodiment, the head portion of the locking member attached to the through-hole of the second belt portion has, on a side near a leading end of the second belt portion in the lengthwise direction, an inclined surface that is inclined in an orientation of being located gradually farther away from the front surface of the second belt portion the farther from the leading end of the second belt portion it is.

With the belt according to this embodiment, in the case of actually mounting the belt on the target object, when the user pulls the leading end of the second belt portion until the head portion of the locking member is past the side of the frame-shaped body, the head portion of the locking member easily goes under the side of the frame-shaped body and easily goes past the side of the frame-shaped body while the side of the frame-shaped body is pushed up by the inclined surface. Accordingly, the belt is smoothly mounted on the target object.

With the belt according to an embodiment, in the head portion of the locking member attached to the through-hole of the second belt portion, a side surface on a side that is far from the leading end of the second belt portion in the lengthwise direction hangs over the opposing front surface of the second belt portion.

With the belt according to this embodiment, in the head portion of the locking member attached to the through-hole of the second belt portion, the side surface on the side that is far from the leading end of the second belt portion in the lengthwise direction hangs over the opposing front surface of the second belt portion. Accordingly, when the belt is mounted on the target object, the side surface of the head portion of the locking member on the side that is far from the leading end of the second belt portion is reliably locked by the side of the frame-shaped body. Accordingly, it is possible to reliably prevent a situation in which the second belt portion unexpectedly comes out of the frame-shaped body.

With the belt according to an embodiment, the shape of the through-hole of the second belt portion has a property in which, when rotated 180 degrees about an axis that passes through the center of the through-hole and is perpendicular to the second belt portion, the shape matches the original shape of the through-hole before rotation, and the shapes of the neck portion and the head portion of the locking member have a property in which, when rotated 180 degrees about the axis, the shapes match the original shapes of the neck portion and the head portion before rotation.

With the belt according to this embodiment, the shape of the through-hole of the second belt portion and the shapes of the neck portion and the head portion of the locking member each have two-fold rotational symmetry about the axis. Accordingly, when the user attaches the locking member to the through-hole formed in the second belt portion, regardless of whether or not the locking member is rotated 180 degrees about the axis, the head portion of the locking member after attachment has an inclined surface that is inclined in an orientation of being located gradually farther away from the front surface of the second belt portion the further from the leading end of the second belt it is, on the side near the leading end of the second portion in the lengthwise direction. Accordingly, the belt is smoothly mounted on the target object. Also, regardless of whether or not there is 180-degree rotation about the axis, the head portion of the locking member after attachment is such that the side surface thereof on the side far from the leading end of the second belt portion along the lengthwise direction hangs over the opposing front surface of the second belt portion. Accordingly, it is possible to reliably prevent a situation in which the second belt portion unexpectedly comes out of the frame-shaped body.

Here, if a set of multiple through-holes is formed at each position in the lengthwise direction of the second belt portion, the through-hole sets have a constant shape that, when rotated 180 degrees about an axis that passes through the center of the through-hole set and is perpendicular to the second belt portion, coincides overall with the original shape of the through-hole set before being rotated. The same follows for the neck portion and the head portion of the locking member.

With the belt according to an embodiment, the shape of the through-hole of the second belt portion has a property in which, when rotated 180 degrees about an axis that passes through the center of the through-hole and is perpendicular to the second belt portion, the shape is different from the original shape of the through-hole before rotation, and the shape of the neck portion of the locking member is substantially the same as the shape of the through-hole.

With the belt according to this embodiment, the shape of the through-hole of the second belt portion has a property in which, when rotated 180 degrees about the axis that passes through the through hole and is perpendicular to the second belt portion, the shape is different from the original shape of the through-hole before rotation. In other words, the rotational symmetry of the shape of the through-hole is not two-fold. The shape of the neck portion of the locking member is substantially the same as the shape of the through-hole. Accordingly, when the user attaches the locking member to the specific through-hole among the multiple through-holes formed in the second belt portion in advance before mounting the belt on the target object, the user is prompted to attach the locking member in an orientation in which the shape of the neck portion of the locking member coincides with the shape of the through-hole, or in other words, in the original orientation. As a result, a case is prevented in which the locking member is erroneously attached in an orientation of being rotated 180 degrees with respect to the original orientation (an attachment error).

Here, if a set of multiple through-holes is formed at each position in the lengthwise direction of the second belt portion, the through-hole sets have a constant shape that, when rotated 180 degrees about an axis that passes through the center of the through-hole set and is perpendicular to the second belt portion, is different overall from the original shape of the through-hole set before rotation. Accordingly, when the user attaches the locking member to the specific through-hole set among the multiple through-hole sets formed in the second belt portion in advance before mounting the belt on the target object, a case is prevented in which the locking member is erroneously attached in an orientation of being rotated 180 degrees with respect to its original orientation (an attachment error).

With the belt according to an embodiment, at each position of the through-holes aligned in the lengthwise direction, the rear surface of the second belt portion has a recessed portion for determining a direction of the locking member about an axis that passes through the center of the through-hole and is perpendicular to the second belt portion, and the base portion of the locking member has a protrusion configured to fit into the recessed portion of the second belt portion only when the locking member is oriented in a specific direction about the axis.

With the present embodiment, the "recessed portion" on the rear surface of the second belt portion need only be recessed, and may be a hole that penetrates through the second belt portion.

With the belt according to this embodiment, when the user attaches the locking member to the specific through-hole among the multiple through-holes formed in the second belt portion in advance before mounting the belt on the target object, the protrusion on the base portion fits into the recessed portion on the rear surface of the second belt portion only when the locking member is oriented in a specific direction about the axis. When the locking member is oriented in another direction about the axis, the protrusion on the base portion does not fit into the recessed portion of the second belt portion, and therefore the base portion does not come into close contact with the rear surface of the second belt portion and attachment cannot be performed reliably. Accordingly, a case is prevented in which the locking member is attached in an orientation that is wrong with regard to its original orientation (an attachment error).

Note that if a set of multiple through-holes is formed at each position in the lengthwise direction of the second belt portion, the "center of the through-holes" refers to the center of a through-hole set.

With the belt according to an embodiment, the base portion of the locking member attached to the through-hole of the second belt portion exists only in a region corresponding to the leading end side of the second belt portion from the neck portion in the lengthwise direction.

With the belt according to the embodiment, the base portion of the locking member attached to the through-hole of the second belt portion exists only in the region corresponding to the leading end side of the second belt portion from the neck portion in the lengthwise direction. In other words, the base portion of the locking member does not exist in the region corresponding to the first belt portion side with respect to the neck portion in the lengthwise direction. Accordingly, when the belt is to be mounted on the wrist of a body, for example, it is possible to avoid an inconvenience in which the tissue (flesh) of the wrist surface is caught between the rear surface of the second belt portion and the base portion of the locking member.

In other words, if the base portion of the locking member exists in a region corresponding to the first belt portion side with respect to the neck portion in the lengthwise direction, when the user passes the second belt portion through the frame-shaped body attached to the first belt portion and pulls the leading end of the second belt portion, the second belt portion warps with a relatively small curvature radius due to the side of the frame-shaped body, and a gap that is open toward the wrist sometimes occurs between the rear surface of the second belt portion and the base portion. When the user releases the leading end of the second belt portion in this state, the gap starts to close, and there is a possibility that tissue (flesh) of the wrist surface will be caught between the rear surface of the second belt portion and the base portion of the locking member. In contrast to this, if the base portion of the locking member does not exist in the region corresponding to the first belt portion side with respect to the neck portion in the lengthwise direction, it is possible to avoid such an inconvenience.

With the belt according to an embodiment, a removal mechanism configured to, in a state in which the belt main body is mounted on the target object, release the locking member locked using the side of the frame-shaped body is included.

With the belt according to the embodiment, in the state in which the belt main body is mounted on the target object, the user can use the removal mechanism to release the locking member locked by the side of the frame-shaped body. Accordingly, it is easy to remove the belt.

With the belt according to an embodiment, a fixing member configured to, in a state in which the belt main body is mounted on the target object, fix a portion of the second portion that is past the side of the frame-shaped body to a corresponding portion of the first belt portion is included.

With the belt according to the embodiment, in the state in which the belt main body is mounted on the target object, the fixing member fixes the portion of the second belt portion that is past the side of the frame-shaped body (includes the leading end) to the portion corresponding to the first belt portion. Accordingly, the belt is reliably mounted on the target object. Also, a case is prevented in which the portion of the second belt portion that is past the side of the frame-shaped body dangles and gets in the way or tarnishes the appearance when the target object moves (i.e., if the target object is a wrist of a body, or the like).

With the belt according to an embodiment, a detection unit configured to detect tensile force of the belt main body is installed.

With the belt according to the embodiment, the mounted detection unit detects the tensile force of the belt main body. Accordingly, the user can be made aware of the tensile force of the belt main body, and can check that the belt main body is suitably mounted on the target object.

The belt according to one or more embodiments of the claimed invention is a belt to be mounted by being wrapped around a substantially rod-shaped target object, including: a belt main body extending in the form of a long, narrow band; a frame-shaped body attached to a first belt portion that corresponds to a side on an end in a lengthwise direction of the belt main body; a plurality of through-holes formed in alignment in the lengthwise direction in a second belt portion corresponding to a side opposite to the first belt portion in the lengthwise direction of the belt main body; and a locking member that is configured separately from the belt main body and is configured to be attached to a through-hole of the second belt portion so as to protrude from a front surface of the second belt portion in advance, before the belt is mounted on the target object, wherein the locking member includes a base portion to be arranged in contact with the rear surface of the second belt, a neck portion that is continuous with the base portion and is to extend through the through hole to the front surface of the second belt portion, and a head portion that is provided on a leading end of the neck portion and has a dimension greater than a dimension of the through hole, in a state in which the belt main body is mounted on a target object, the second belt portion is passed through the frame-shaped body, and a side of the frame-shaped body locks the head portion of the locking member so as to prevent the second belt portion from coming out of the frame-shaped body, the shape of the through-hole of the second belt portion has a property in which, when rotated 180 degrees about an axis that passes through the center of the through-hole and is perpendicular to the second belt portion, the shape differs from the original shape of the through-hole before rotation, and the shape of the neck portion of the locking member is substantially the same as the shape of the through-hole, and thus the locking member is allowed to be attached in an original orientation in which the shape of the neck portion matches the shape of the through-hole, while the locking member is not allowed to be attached in a wrong orientation of being rotated 180 degrees about the axis.

According to one or more embodiments of the claimed invention, the belt is a belt to be mounted by being wrapped around a substantially rod-shaped target object, including: a belt main body that extends in the form of a long, narrow band; a frame-shaped body attached to a first belt portion that corresponds to a side on an end in a lengthwise direction of the belt main body; a plurality of through-holes formed in alignment in the lengthwise direction in a second belt portion corresponding to a side opposite to the first belt portion in the lengthwise direction of the belt main body; and a locking member that is configured separately from the belt main body and is configured to be attached to a through-hole of the second belt portion so as to protrude from a front surface of the second belt portion in advance, before the belt is mounted on the target object, wherein the locking member includes a base portion to be arranged in contact with the rear surface of the second belt, a neck portion that is continuous with the base portion and is to extend through the through hole to the front surface of the second belt portion, and a head portion that is provided on a leading end of the neck portion and has a dimension greater than a dimension of the through hole, in a state in which the belt main body is mounted on a target object, the second belt portion is passed through the frame-shaped body, and a side of the frame-shaped body locks the head portion of the locking member so as to prevent the second belt portion from coming out of the frame-shaped body, at each position of the through-holes aligned in the lengthwise direction, the rear surface of the second belt portion has a recessed portion for determining a direction of the locking member about an axis that passes through the center of the through-hole and is perpendicular to the second belt portion, and the base portion of the locking member has a protrusion that fits into the recessed portion of the second belt portion only when the locking member is oriented in a specific direction about the axis.

According to one or more embodiments of the claimed invention, the belt is a belt to be mounted by being wrapped around a substantially rod-shaped target object, including: a belt main body that extends in the form of a long, narrow band; a frame-shaped body attached to a first belt portion that corresponds to a side on an end in a lengthwise direction of the belt main body; a plurality of through-holes formed in alignment in the lengthwise direction in a second belt portion corresponding to a side opposite to the first belt portion in the lengthwise direction of the belt main body; and a locking member that is configured separately from the belt main body and is configured to be attached to a through-hole of the second belt portion so as to protrude from a front surface of the second belt portion in advance, before the belt is mounted on the target object, wherein the locking member includes a base portion to be arranged in contact with the rear surface of the second belt, a neck portion that is continuous with the base portion and is to extend through the through hole to the front surface of the second belt portion, and a head portion that is provided on a leading end of the neck portion and has a dimension greater than a dimension of the through hole, in a state in which the belt main body is mounted on a target object, the second belt portion is passed through the frame-shaped body, and a side of the frame-shaped body locks the head portion of the locking member so as to prevent the second belt portion from coming off of the frame-shaped body, and the base portion of the locking member attached to the through-hole of the second belt portion exists only in a region corresponding to the leading end side of the second belt portion from the neck portion in the lengthwise direction, which prevents a surface of the target object from being caught between the second belt portion and the base portion of the locking member when a portion of the second belt portion that is passed through the frame-shaped body and to which the locking member is attached is wrapped around the side of the frame-shaped body and bent in a process in which the belt is mounted on the target object.

Also, a wearable device according to one or more embodiments of the claimed invention includes: the belt according to one or more embodiments of the claimed invention; and a device to be mounted on a body using the belt.

With the wearable device according to one or more embodiments of the claimed invention, it is possible to appropriately set the tensile force of the belt main body in the state of being mounted on the body. Accordingly, when the device mounted on the body using the belt includes the function of an activity level meter or a pulse meter, for example, the measurement accuracy relating to that function can be increased.

It is preferable that the above-described device is integrally built into the belt main body or is attached to the belt main body. In this case, it is easy to mount the device on the body.

Advantageous Effects of Invention

As is clear from the above description, with the belt according to one or more embodiments of the claimed invention, the tensile force of the belt main body in the state of being mounted on the target object can be set appropriately.

Also, with the wearable device according to one or more embodiments of the claimed invention, it is possible to appropriately set the tensile force of the belt main body in the state of being mounted on the body.

DESCRIPTION OF EMBODIMENTS

Hereinafter, embodiments of the invention will be described in detail with reference to the drawings.

Figure 1:
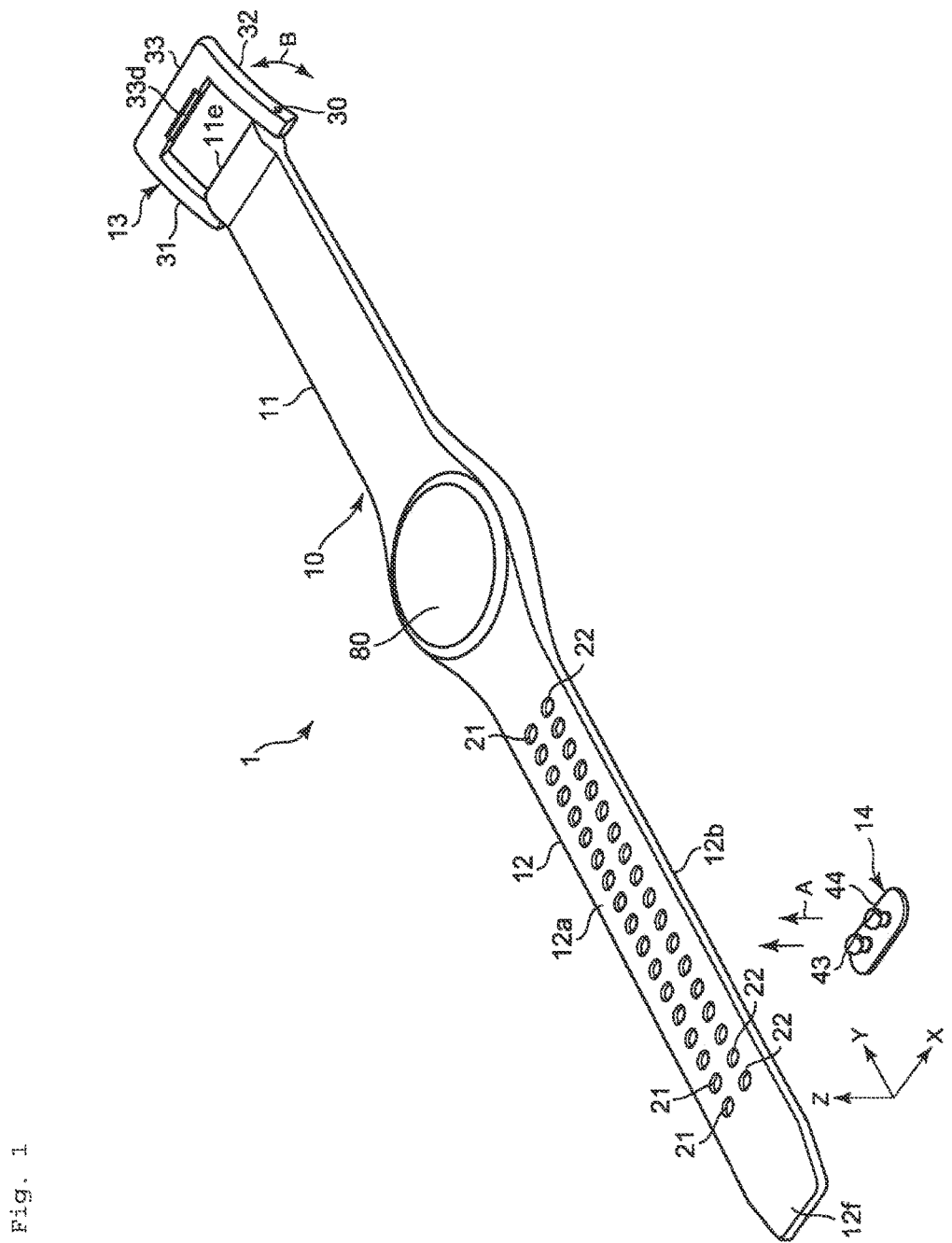
FIG. 1 is a diagram showing a perspective view of a wearable device according to an embodiment, to which a belt according to one or more embodiments of the claimed invention has been applied.

FIG. 1 shows a perspective view of a wearable device 1 according to an embodiment of the invention. The wearable device 1 includes a belt (hereinafter referred to as "belt main body") 10 that extends in the form of a long, narrow band, and a device 80 that is to be mounted on a wrist of a body by the belt main body 10. In this example, the device 80 includes the function of an activity level meter or a pulse meter. Note that for the sake of convenience in the description, an XYZ orthogonal coordinate system is shown as well.

The belt main body 10 is composed of flexible silicone resin (a modulus that expresses elasticity being 20 to 65 [MPa]), and includes a first belt portion 11 that corresponds to a side (+Y side) on an end in the Y direction, which serves as the lengthwise direction, and a second belt portion 12 that corresponds to the side (−Y side) opposite to the first belt portion 11 in the Y direction. The device 80 is integrally built-in between the first belt portion 11 and the second belt portion 12.

An approximately rectangular ring 13 serving as the frame-shaped body is attached to an end portion 11e on the side of the first belt portion 11 that is far from the device 80 (i.e., the +Y side). The ring 13 is composed of a coupling rod (a known spring rod) 30 that is provided so as to penetrate through the end portion 11e of the first belt portion 11 in the X direction (direction along the belt surface, orthogonal to the lengthwise direction of the belt), and an approximately U-shaped member (the three sides of the U-shaped member being denoted by reference numerals 31, 32, and 33), which is attached to the coupling rod 30 so as to be able to rotate as indicated by the double-sided arrow B. The side (side corresponding to the side opposite to the coupling rod 30) 33 in the center of the U-shaped member has an edge portion 33d that is thinner than the other portions, on a side near the coupling rod 30. The thickness of the edge portion 33d is set to be about the same as the heights of contact surfaces 43a and 44a of the head portions 43 and 44, such that it is easy to lock the head portions 43 and 44 of the later-described locking member 14. In this example, the ring 13 is composed of a metal material, but it may be composed of a plastic material.

In this example, sets of two through-holes 21 and 22 (referred to as "through-hole sets 21, 22") are formed in alignment in the Y direction on the second belt portion 12. That is, a column of through-holes 21 on the −X side and a column of through-holes 22 on the +X side are formed. In this example, as shown in the planar layout in FIG. 6, the through-holes 21 and 22 that form the sets are each formed in the same oval shape. Also, the through-hole sets 21, 22; 21, 22; . . . at each position along the Y direction have the same shape as each other. The pitch at which the through-hole sets 21, 22 are aligned in the Y direction is constant in this example, but may be made variable according to the region in the Y direction.

Figure 3:
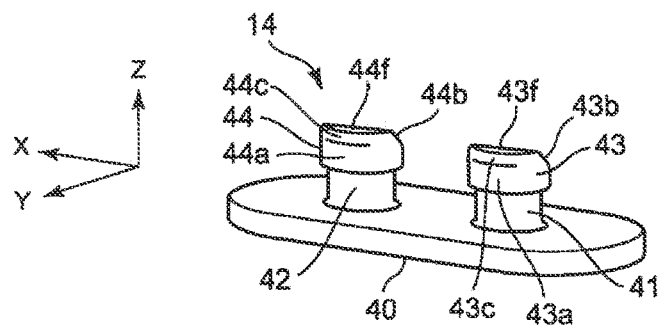
FIG. 3 is a perspective view showing the locking member.

The locking member 14 shown in FIG. 1 is attached to a through-hole set 21, 22 of the second belt portion 12. As shown in FIG. 3 (perspective view), FIG. 4 (plan view), and FIG. 5 (side view), the locking member 14 has a shared base portion 40, two neck portions 41 and 42 that are continuous with the base portion 40 and correspond to the through-hole sets 21, 22, and head portions 43 and 44 that are provided on the leading ends of the neck portions 41 and 42. In this example, the locking member 14 is composed of an integrally-formed plastic material (e.g., ABS resin or the like), but it may be composed of metal.

The base portion 40 has a mode of being a flat plate with an oval shape. The neck portions 41 and 42 have a mode of being columns that are continuous with the base portion 40 and have oval-shaped cross-sections. The shapes and dimensions of the neck portions 41 and 42 are set to be substantially the same as the respective shapes and dimensions of the through-holes 21 and 22. The head portions 43 and 44 have a mode of being columns with oval-shaped cross-sections with dimensions larger than the dimensions of the through-holes 21 and 22. More specifically, on the upper side (+Z side), the head portions 43 and 44 include, in the following order: inclined surfaces 43b and 44b, which are inclined in an orientation of being located gradually farther away from the base portion 40 as the +Y side is approached from the −Y side, flat surfaces 43f and 44f that are continuous with the inclined surfaces 43b and 44b and are parallel to the base portion 40, and brim portions 43c and 44c that are continuous with the flat surfaces 43f and 44f and protrude toward the +Y side from the side surfaces (surfaces of contact with the side 33 of the ring 13) 43a and 44a on the near side (+Y side) in FIG. 3.

Figure 2:
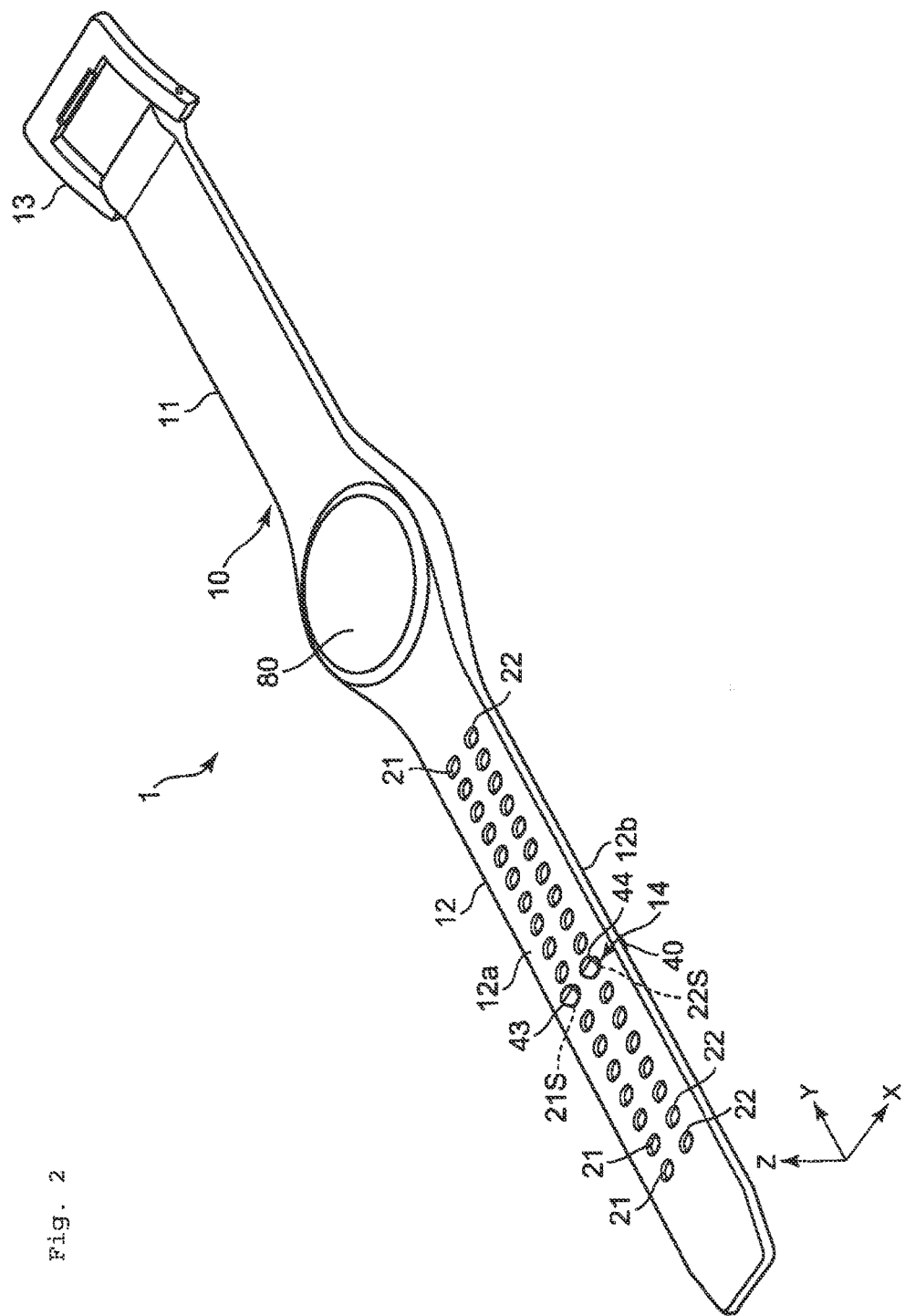
FIG. 2 is a perspective view showing a state in which a locking member is attached to a specific through-hole set of a second belt portion of the wearable device.
Figure 6:
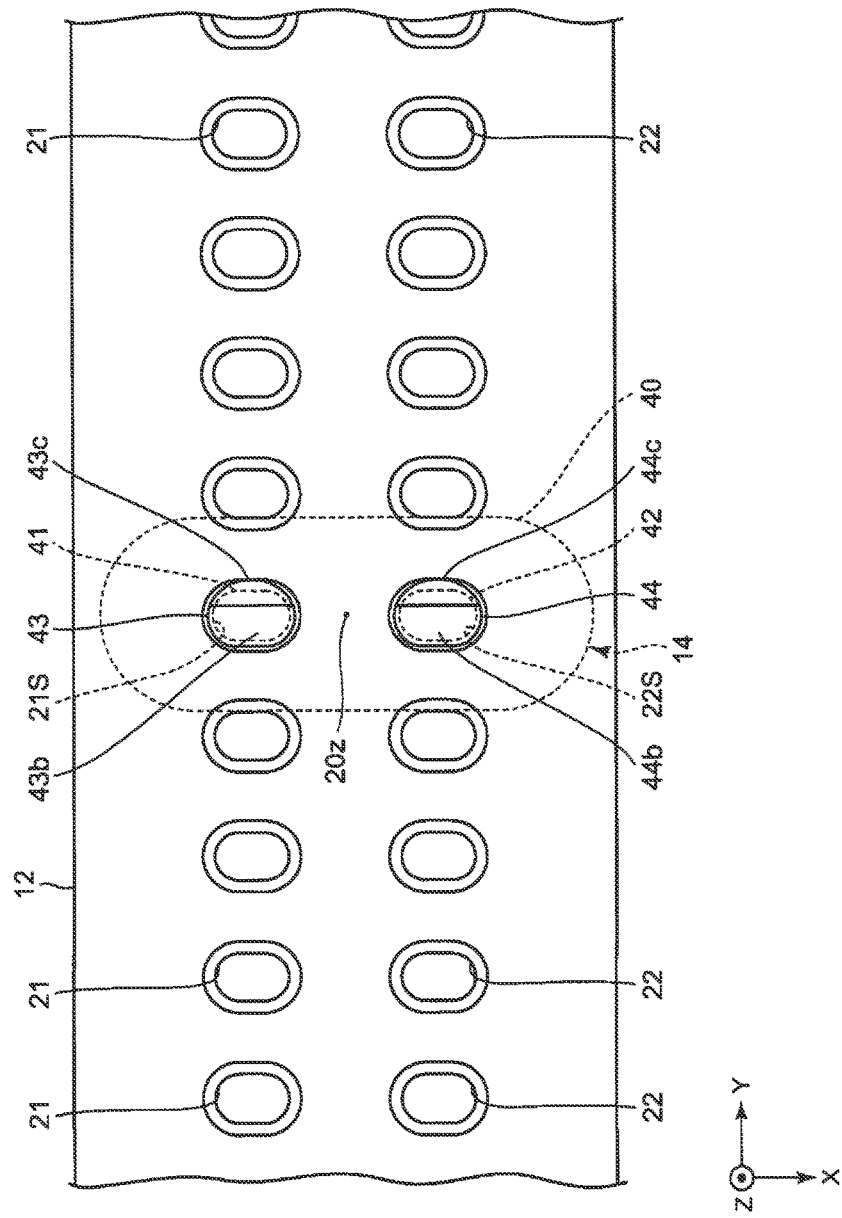
FIG. 6 is a planar layout view showing a state in which the locking member is attached to a specific through-hole set of the second belt portion.

As shown in FIGS. 2 and 6, when the wearable device 1 is to be mounted on the wrist 90 serving as the target object, the user attaches the locking member 14 to a specific through-hole set (indicated by reference numerals 21S and 22S) among the multiple through-hole sets 21, 22 formed in the second belt portion 12 of the belt main body 10 in advance, such that the head portions 43 and 44 protrude from the front surface of the second belt portion 12.

For example, as indicated by the arrow A in FIG. 1, the user presses the head portions 43 and 44 of the locking member 14 through the through-hole set 21S, 22S from the rear surface 12b side of the second belt portion 12, whereby the locking member 14 is easily attached to the through-hole set 21S, 22S. The head portions 43 and 44 of the locking member 14 have dimensions that are larger than the dimensions of the through-hole set 21S, 22S, and therefore once the locking member 14 is attached to the through-hole set 21S, 22S as shown in FIGS. 2 and 6, the locking member 14 does not naturally detach therefrom. The mode of attaching the locking member 14 is a mode in which the base portion 40 is in contact with the rear surface 12b of the second belt portion 12, the neck portions 41 and 42 extend through the through-hole set 21S, 22S to the front surface 12a of the second belt portion 12, and the head portions 43 and 44 protrude in an outward direction (+Z direction) from the front surface 12a.

When the locking member 14 is attached to the through-hole set 21S, 22S, the inclined surfaces 43b and 44b of the head portions 43 and 44 of the locking member 14 enter a state of being located gradually farther away from the front surface 12a of the second belt portion 12 as the first belt portion 11 is approached from the leading end 12f of the second belt portion 12 in the Y direction (forward-tapered state).

Figure 7:
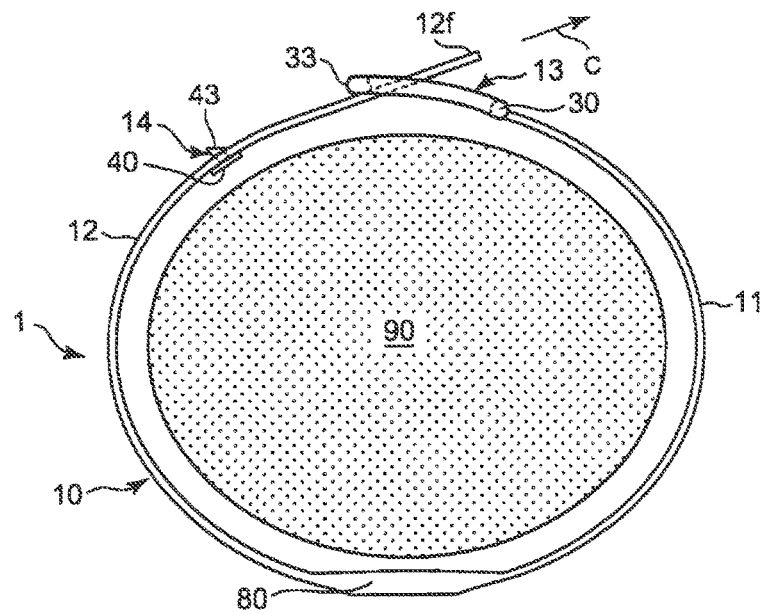
FIG. 7 is a diagram illustrating how the wearable device is mounted on a wrist.
Figure 8:
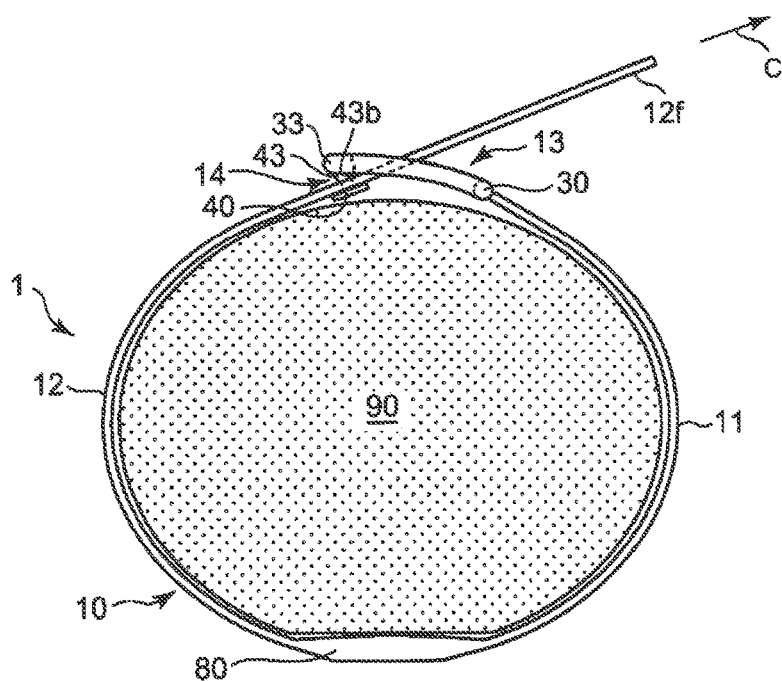
FIG. 8 is a diagram illustrating how the wearable device is mounted on a wrist.
Figure 9:
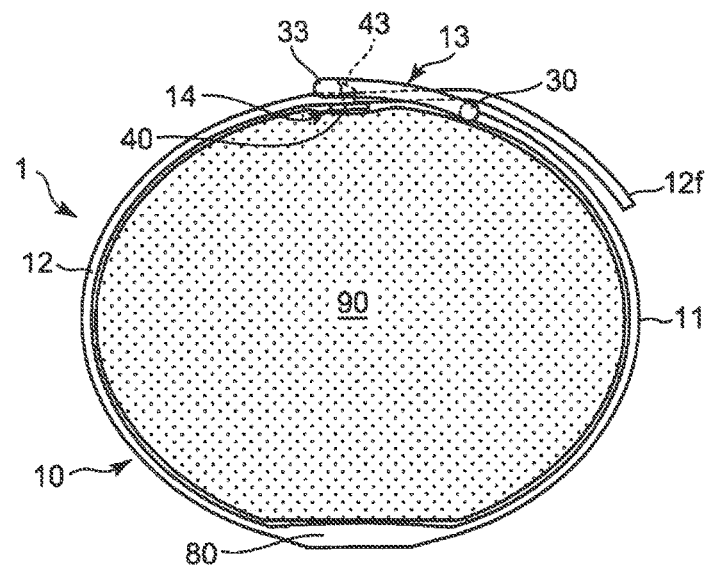
FIG. 9 is a diagram illustrating how the wearable device is mounted on a wrist.

When the wearable device 1 is to be actually mounted on the wrist 90, as shown in FIG. 7, the user first passes the leading end 12f of the second belt portion 12 through the ring 13 attached to the first belt portion 11 as indicated by the arrow C in FIG. 7, so as to wrap the belt main body 10 around the wrist 90. Next, as shown in FIG. 8, the user pulls the leading end 12f of the second belt portion 12 in the direction indicated by the arrow C in FIG. 8 until the head portion 43 (and 44) of the locking member 14 goes past the side 33 of the ring 13, and then the user releases the leading end 12f. Upon doing so, as shown in FIG. 9, the side 33 of the ring 13 locks the head portion 43 (and 44) of the locking member 14, thereby preventing the second belt portion 12 from slipping through the ring 13. Thus, the wearable device 1 is mounted on the wrist 90.

Here, when the user pulls the leading end 12f of the second belt portion 12 in the direction indicated by the arrow C in FIG. 8 until the head portions 43 and 44 of the locking member 14 are past the side 33 of the ring 13, the inclined surfaces 43b and 44b of the head portions 43 and 44 of the locking member 14 enter the forward-tapered state. Accordingly, the head portions 43 and 44 of the locking member 14 easily go under the side 33 of the ring 13 and easily go past the side 33 of the ring 13 while the side 33 of the 13 is pushed up by the inclined surfaces 43b and 44b. Accordingly, the belt is smoothly mounted on the wrist 90.

Figure 10:
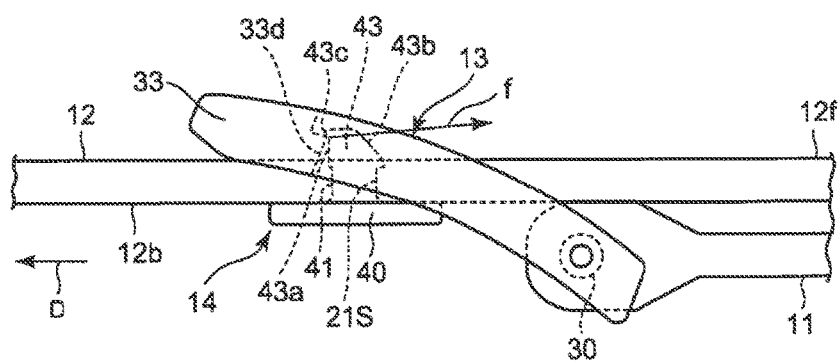
FIG. 10 is an enlarged diagram showing a situation in which a side of a ring locks a head portion of the locking member in a state in which the belt main body is mounted on the wrist.

In the state in which the belt main body 10 is mounted on the wrist 90, the side 33 of the ring 13 locks the head portions 43 and 44 of the locking member 14. Here, as shown in FIG. 10, the head portions 43 and 44 of the locking member 14 receive a force f from the side 33 of the ring 13 toward, approximately, the leading end 12f of the second belt portion 12 in the Y direction. The force f is received due to the neck portions 41 and 42 being supported by the through-hole set 21S, 22S and the base portion 40 being supported by the rear surface 12b of the second belt portion 12. Accordingly, the locking member 14 does not come off of the second belt portion 12 due to the force received from the side 33 of the ring 13.

Also, on the head portions 43 and 44 of the locking member 14, the side surfaces (contact surfaces) 43a and 44a on the side far from the leading end 12f of the second belt portion 12 in the Y direction substantially hang over the opposing front surface 12a of the second belt portion 12, due to the presence of the brim portions 43c and 44c. Also, as stated above, the thickness of the edge portion 33d of the side 33 of the ring is set to be approximately the same as the heights of the contact surfaces 43a and 44a of the head portions 43 and 44, so that it is easier to lock the head portions 43 and 44 of the locking member 14. Accordingly, in the state in which the belt main body 10 is mounted on the wrist 90, the contact surfaces 43a and 44a of the head portions 43 and 44 of the locking member 14 are reliably locked by the side 33 (in this example, the edge portion 33d) of the ring 13. Accordingly, a situation in which the second belt portion 12 unintentionally slips out from the ring 13 in the direction indicated by arrow D can be reliably prevented.

As described above, with the wearable device 1, the locking member 14 is attached to a specific through-hole set 21S, 22S in the second belt portion 12 of the belt main body 10 in advance before being mounted on the wrist 90. Accordingly, in the state in which the belt main body 10 is mounted on the wrist 90, the length in the circumferential direction from the side 33 of the ring 13 to the locking member 14 (head portions 43 and 44 of the locking member 14) is stable, and the tensile force of the belt main body 10 is appropriately set. As a result, when the device 80 includes the function of an activity level meter or a pulse meter as in this example, measurement is performed stably by the device 80.

As the specific through-hole set 21S, 22S to which the locking member 14 is attached in the above-described second belt portion 12, it is desirable to select a through-hole set that overlaps with the side 33 of the ring 13 when the belt main body 10 is wrapped around the wrist 90 with a certain tensile force (encompasses the case where the tensile force is substantially zero) that is suitable for the function of the device 80, for example. Accordingly, in the state in which the belt main body 10 is mounted on the wrist 90, the belt main body 10 is wrapped around the wrist 90 with that tensile force, or in other words, with a tensile force that is suitable for the function of the device 80.

Also, in this example, the through-hole sets 21, 22; 21, 22; . . . at each position along the Y direction of the second belt portion 12 have the same shape as each other. Accordingly, it is possible to use (attach) the same locking member 14 for the multiple through-hole sets 21, 22; 21, 22; . . . .

Modified Example 1

In the example above, the shapes of the through-hole sets 21, 22 of the second belt portion 12 match the original shapes of through-holes before rotation when rotated 180 degrees about an axis 20z (see FIG. 6), which passes through the center of the through-hole set 21, 22 and is perpendicular to the second belt portion 12. Similarly, the shapes of the neck portions 41 and 42 of the locking member 14 match the original shapes of the neck portions before rotation when rotated 180 degrees about an axis. In other words, the shapes of the through-hole sets 21, 22 and the neck portions 41 and 42 have two-fold rotational symmetry about the axis 20z. For this reason, a situation (attachment error) is envisioned in which the locking member 14 is attached rotated 180 degrees about the axis 20z with respect to the original orientation when the user attaches the locking member 14 to the through-hole sets 21, 22 of the second belt portion 12. If such an attachment error occurs, in the above-described example, in the case where the belt is actually mounted on the wrist 90, there is a possibility that the head portions 43 and 44 of the locking member 14 will catch on the side 33 of the ring 13 and prevent smooth mounting when the user pulls the leading end 12f of the second belt portion 12 in the direction indicated by the arrow C in FIG. 8 until the head portions 43 and 44 of the locking member 14 go past the side 33 of the ring 13. Also, in the state in which the belt is mounted on the wrist 90, there is a possibility that the head portions 43 and 44 of the locking member 14 will go under the side 33 of the ring 13 due to the inclined surfaces 43b and 44b, which helps the second belt portion 12 come out from the ring 13.

Figure 4:
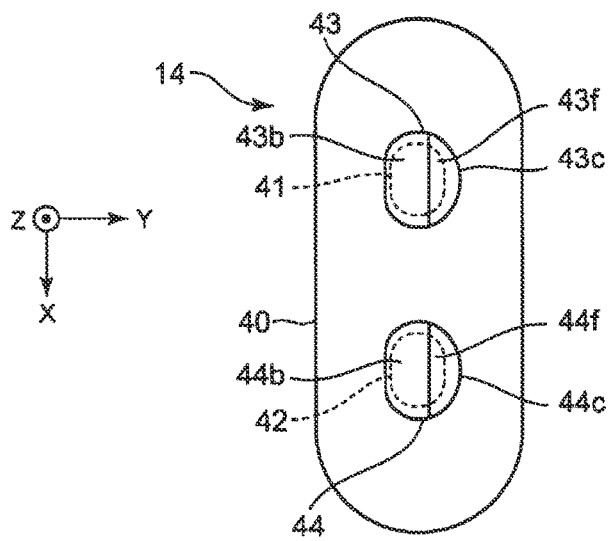
FIG. 4 is a plan view showing the locking member.
Figure 11:
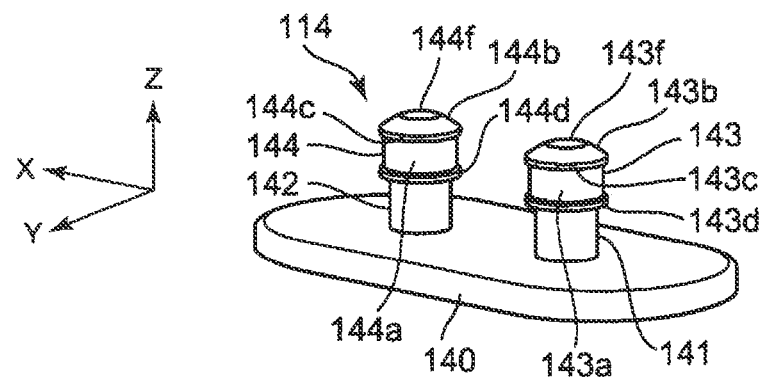
FIG. 11 is a perspective view showing a locking member of Modified Example 1.
Figure 12:
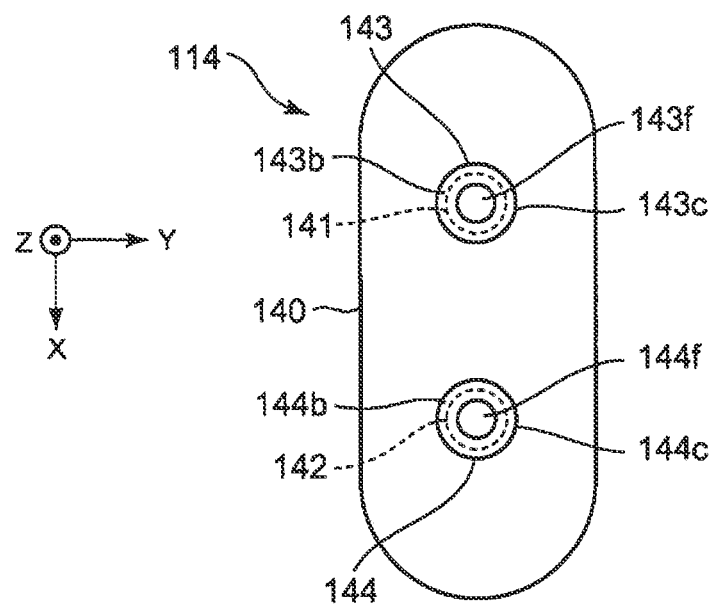
FIG. 12 is a plan view showing the locking member of Modified Example 1.

A modified example of the above-described locking member 14 and the second member 12, in which a countermeasure against such a situation has been carried out, will be described with reference to FIGS. 11, 12, and 13 (the locking member and second belt portion of the modified example are denoted by reference numerals 114 and 112 respectively). Note that in FIGS. 11, 12, and 13, elements corresponding to the elements in FIGS. 3, 4, and 6 are denoted by reference numerals that have been increased by 100 (accordingly, redundant description is omitted as appropriate).

Figure 13:
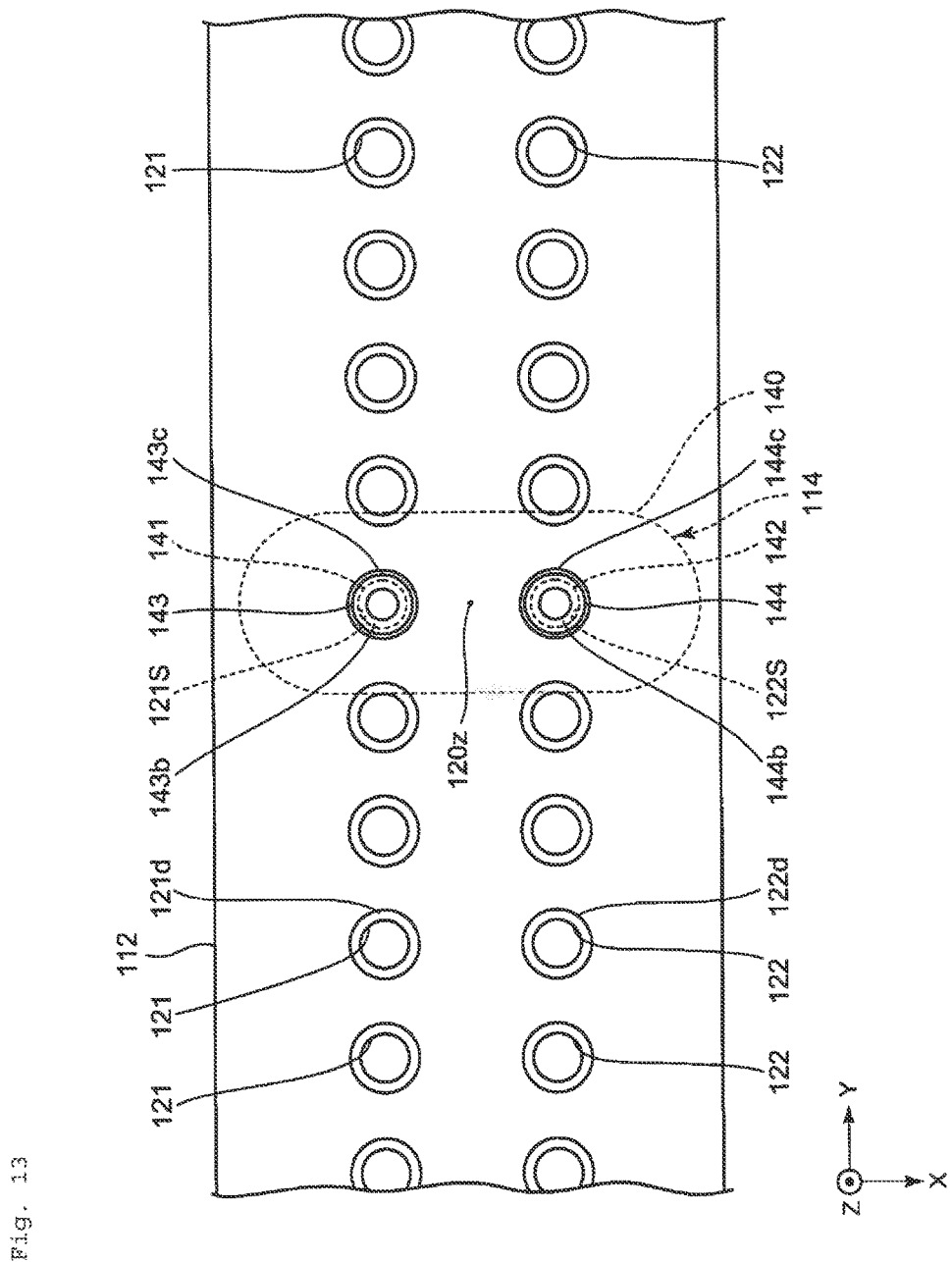
FIG. 13 is a planar layout diagram showing a state in which the locking member of Modified Example 1 is attached to a specific through-hole set of the second belt portion.

Through-holes 121 and 122 that form sets at each position along the Y direction are formed in the second belt portion 112 in circular shapes that are the same as each other, as shown in the planar layout in FIG. 13. In other words, the shape of the through-hole set 121, 122 of the second belt portion 112 has two-fold rotational symmetry about an axis 120z that passes through the center of the through-hole set 121, 122 and is perpendicular to the second belt portion 112, similarly to the previous example.

With the locking member 114, the shapes and dimensions of the neck portions 141 and 142 are set to be substantially the same as the shapes and dimensions of the through-holes 121 and 122. As can be understood according to FIGS. 11 and 12, the head portions 143 and 144 have a mode of roughly being cylindrical columns that have dimensions greater than the dimensions of the through-hole sets 121, 122. More specifically, the head portions 143 and 144 include, on the upper side (+Z side), in the following order: flat surfaces 143f and 144f that are parallel to the base portion 140, truncated conical surfaces 143b and 144b that are continuous with the flat surfaces 143f and 144f and approach the base portion 140 side (−Z side) while gradually opening the further they are from the flat surfaces 143f and 144f, and ring-shaped brim portions 143c and 144c that protrude outward from the side surfaces (surfaces with which the side 33 of the ring 13 comes into contact) 143a and 144a. The truncated conical surfaces 143b and 144b each constitute surfaces that are inclined in both the −Y direction and the +Y direction. Also, on the lower side (−Z side), the head portions 143 and 144 have vertically-symmetrical ring-shaped protruding portions 143d and 144d on the brim portions 143c and 144c. As can be understood, with the locking member 114, not only the neck portions 141 and 142, but also the head portions 143 and 144 have two-fold symmetry about the axis 120z in FIG. 13.

When the wearable device 1 is to be mounted on the wrist 90 serving as the target object, as shown in FIG. 13, the user attaches the locking member 114 to the specific through-hole set 121S, 122S among the multiple through-hole sets 121, 122 formed in the second belt portion 112 of the belt main body 10 in advance such that the head portions 143 and 144 protrude from the front surface of the second belt portion 112. At this time, the protruding portions 143d and 144d on the lower side are accommodated in chamferings 121d and 122d of the through-hole set 121, 122.

When the locking member 114 is attached to the through-hole set 121S and 122S, regardless of whether or not the locking member 114 has been rotated 180 degrees about the axis 120z, the −Y-side portions of the truncated conical surfaces 143b and 144b of the head portions 143 and 144 of the locking member 114 enter a state of being located gradually farther away from the front surface 112a of the second belt portion 112 as the first belt portion 11 is approached from the leading end 112f of the second belt portion 112 in the Y direction (forward-tapered state).

In the case of actually mounting the wearable device 1 on the wrist 90, when the user pulls the leading end 112f of the second belt portion 112 until the head portions 143 and 144 of the locking member 114 are past the side 33 of the ring 13, similarly to the direction indicated by arrow C in FIG. 8, the −Y-side portion of the truncated conical surfaces 143b and 144b of the head portions 143 and 144 of the locking member 114 enter the forward-tapered state. Accordingly, the head portions 143 and 144 of the locking member 114 easily go under the side 33 of the ring 13 and easily go past the side 33 of the ring 13 while the side 33 of the 13 is pushed up by the truncated conical surfaces 143b and 144b (the −Y-side portions of the truncated conical surfaces 143b and 144b). Accordingly, the wearable device 1 is smoothly mounted on the wrist 90.

Also, in the state in which the belt main body 10 is mounted on the wrist 90, the side 33 of the ring 13 locks the head portions 143 and 144 of the locking member 114. Here, regardless of whether or not the locking member 114 has been rotated 180 degrees about the axis 120z, the head portions 143 and 144 of the locking member 114 are such that side surfaces (contact surfaces) 143a and 144a on the side far from the leading end 112f of the second belt portion 112 in the Y direction substantially hang over the opposing front surface 112a of the second belt portion 112 due to the presence of brim portions 143c and 144c. Accordingly, in the state in which the belt main body 10 is mounted on the wrist 90, the contact surfaces 143a and 144a of the head portions 143 and 144 of the locking member 114 are reliably locked by the side 33 (in this example, the edge portion 33d) of the ring 13. Accordingly, a situation in which the second belt portion 112 unintentionally comes out of the ring 13 can be reliably prevented.

Modified Example 2

Figure 14:
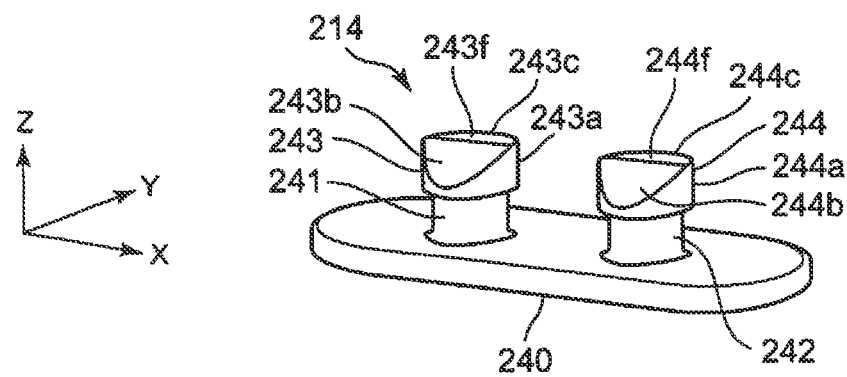
FIG. 14 is a perspective view showing a locking member of Modified Example 2.
Figure 15:
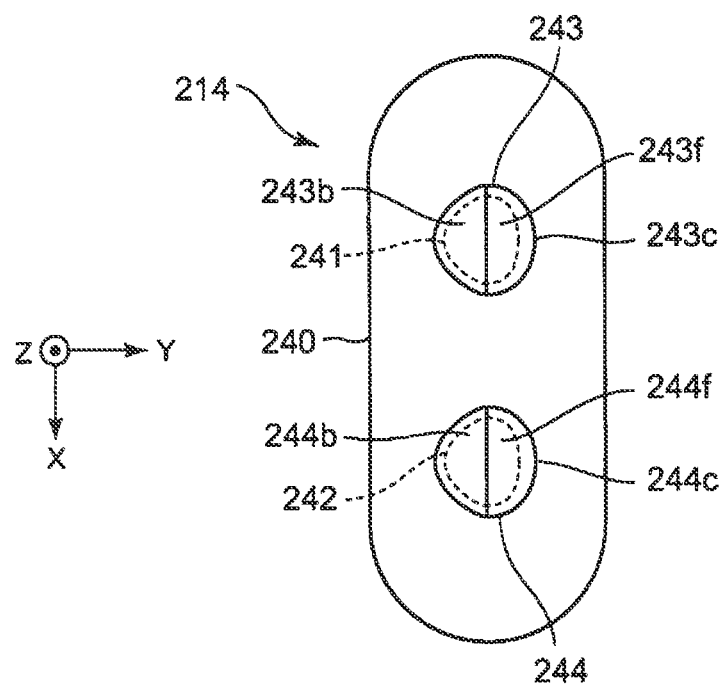
FIG. 15 is a plan view showing the locking member of Modified Example 2.

Another modified example of the above-described locking member 14 and second belt portion 12 will be described with reference to FIGS. 14, 15, and 16 (the locking member and second belt portion of the modified example are denoted by reference numerals 214 and 212 respectively). Note that in FIGS. 14, 15, and 16, elements corresponding to the elements in FIGS. 3, 4, and 6 are denoted by reference numerals that have been increased by 200 (accordingly, redundant description is omitted as appropriate).

Figure 16:
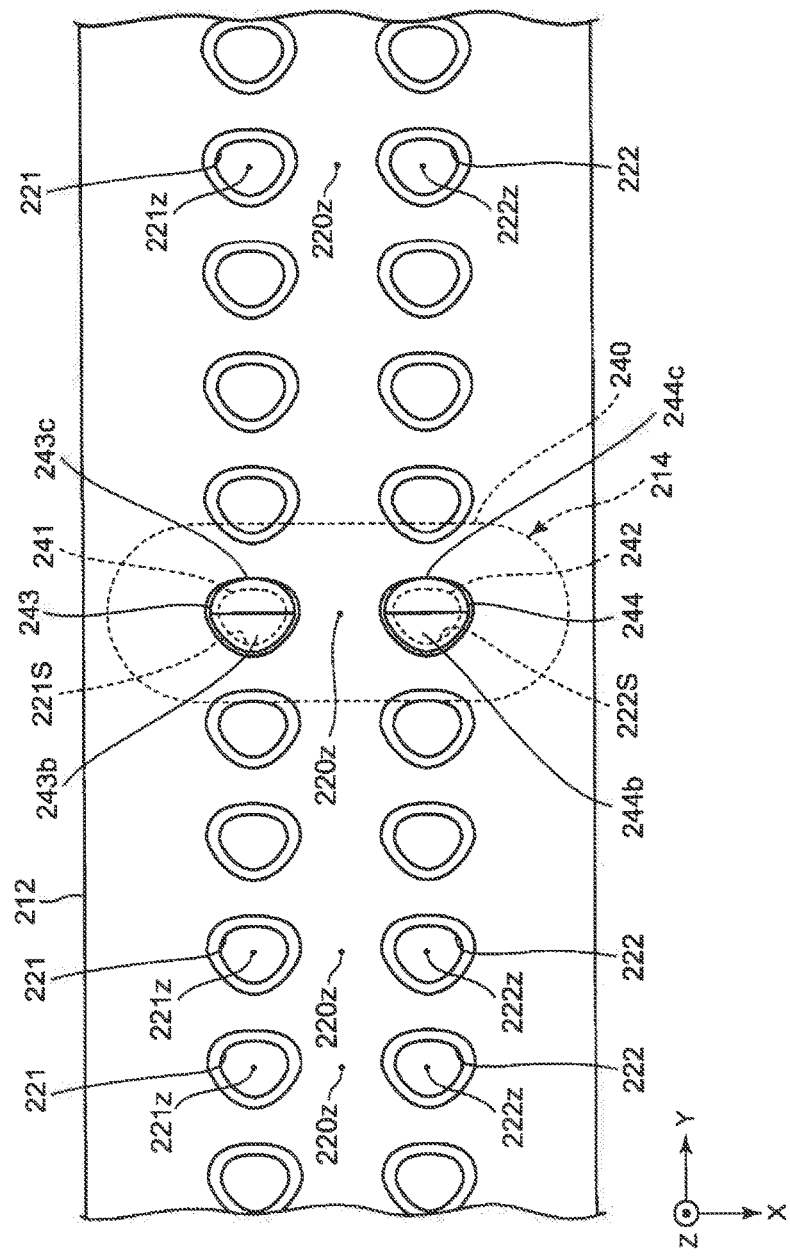
FIG. 16 is a planar layout diagram showing a state in which the locking member of Modified Example 2 is attached to a specific through-hole set of the second belt portion.

Through-holes 221 and 222 that form sets at each position along the Y direction are formed in the second belt portion 212 in triangular shapes with rounded corners that are the same as each other, as shown in the planar layout in FIG. 16. One of the corners (vertices) with a rounded shape of each of the through-holes 221 and 222 faces the −Y direction. The other corners (vertices) of the shapes of the through-holes 221 and 222 face the ±X directions. In other words, the shapes of the through holes 221 and 222 of the second belt portion 212 have a property in which, when rotated 180 degrees about axes 221z and 222z that pass through the centers of the through-holes 221 and 222 and are perpendicular to the second belt portion 212, the shapes are different from the original shapes of the through-holes 221 and 222 before rotation. Accompanying this, the shapes of the through-hole sets 221, 222 also have a property in which, when rotated 180 degrees about an axis 220z that passes through the center of the through-hole set 221, 222 and is perpendicular to the second belt portion 212, the shapes are different from the original shapes of the through-hole sets 221 and 222 before rotation. That is, the rotational symmetry of the shape of the through-hole set 221, 222 is not two-fold.

With the locking member 214, the shapes and dimensions of the neck portions 241 and 242 are set to be substantially the same as the shapes and dimensions of the through-holes 221 and 222. As can be understood from FIGS. 14 and 15, the shapes and dimensions of the head portions 243 and 244 are set to be the same as the shapes and dimensions of the head portions 43 and 44 of the locking member 14 shown in FIGS. 3, 4, and 6.

In such a case, as shown in FIG. 16, when the user attaches the locking member 214 to the specific through-hole set 221S, 222S among the multiple through-hole sets 221, 222 formed in the second belt portion 212 in advance before mounting the wearable device 1 on the wrist 90, the user is prompted to attach the locking member 214 in an orientation in which the shapes of the neck portions 241 and 242 of the locking member 214 match the shapes of the through-hole set 221S, 222S, or in other words, in the original orientation. As a result, a case in which the locking member 214 is erroneously attached in an orientation of being rotated 180 degrees with respect to the original orientation (an attachment error) is prevented.

Modified Example 3

Figure 17:
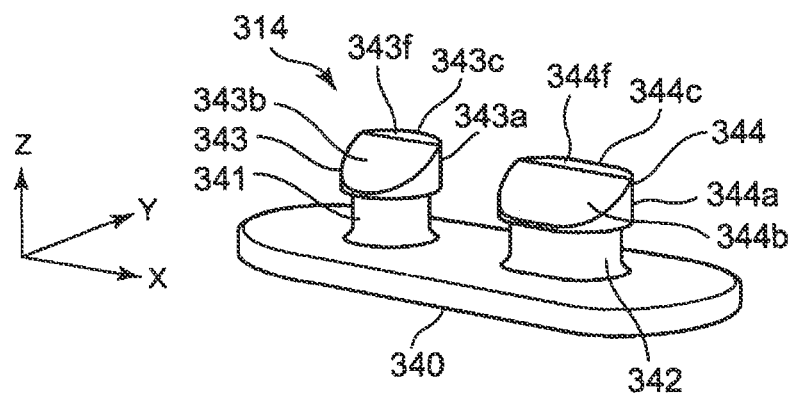
FIG. 17 is a perspective view showing a locking member of Modified Example 3.
Figure 18:
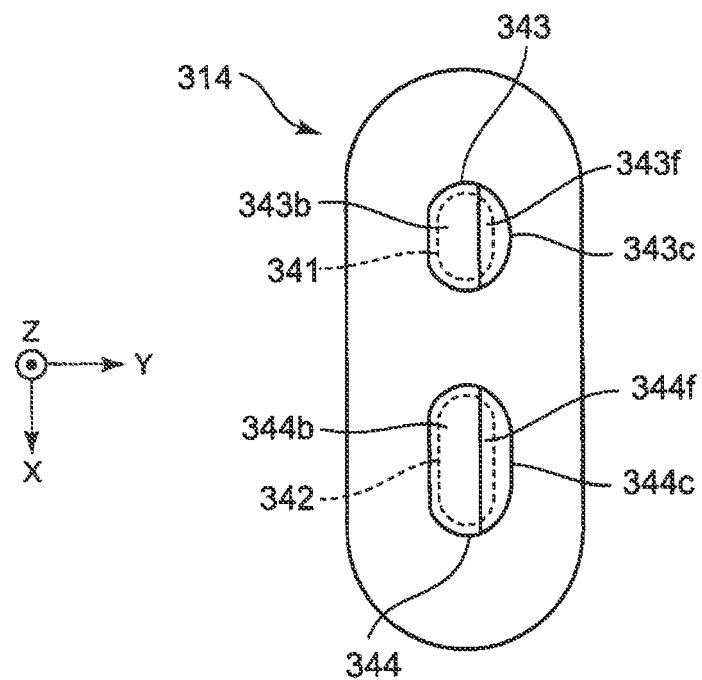
FIG. 18 is a plan view showing the locking member of Modified Example 3.

Another modified example of the above-described locking member 14 and second belt portion 12 will be described with reference to FIGS. 17, 18, and 19 (the locking member and second belt portion of the modified example are denoted by reference numerals 314 and 312 respectively). Note that in FIGS. 17, 18, and 19, elements corresponding to the elements in FIGS. 3, 4, and 6 are denoted by reference numerals that have been increased by 300 (accordingly, redundant description is omitted as appropriate).

Figure 19:
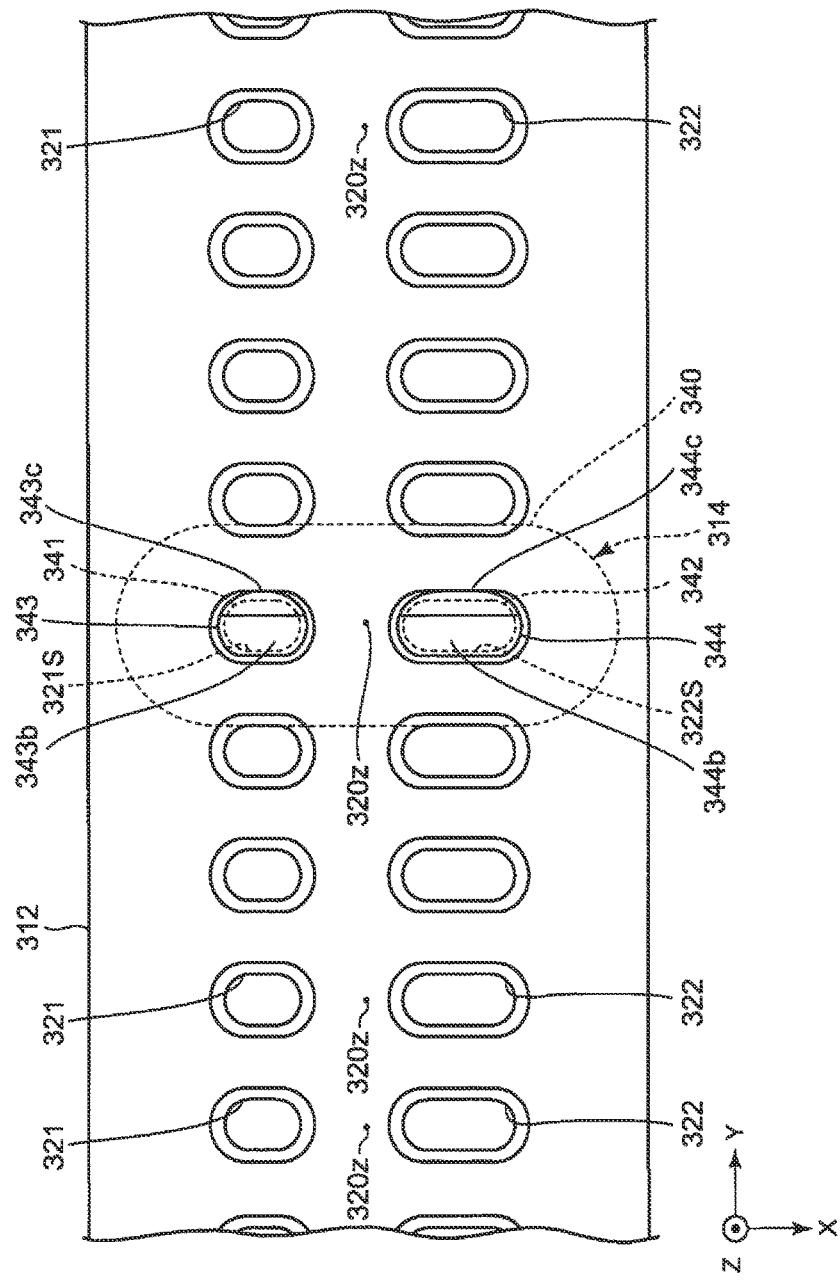
FIG. 19 is a planar layout diagram showing a state in which the locking member of Modified Example 3 is attached to a specific through-hole set of the second belt portion.

Through-holes 321 and 322 that form sets at each position along the Y direction are formed in the second belt portion 312 in oval shapes that are different from each other, as shown in the planar layout in FIG. 19. Specifically, the through-holes 321, which are aligned on the −X side in the second belt portion 312, are set to have the same shape and dimensions as the through-holes 21 of the second belt portion 12 shown in FIG. 6. The through-holes 322, which are aligned on the +X side in the second belt portion 312, are set to be oval shapes whose X-direction dimensions are larger than those of the through-holes 22 (and accordingly, the through-holes 21) of the second belt portion 12 shown in FIG. 6. As a result, the shapes of the through-hole sets 321 and 322 have a property in which, when rotated 180 degrees about an axis 320z that passes through the center of the through-hole set 321, 322 and is perpendicular to the second belt portion 312, the shape is different from the original shapes of the through-hole sets 321 and 322. That is, the rotational symmetry of the shape of the through-hole set 321, 322 is not two-fold.

With the locking member 314, the shapes and dimensions of the neck portions 341 and 342 are set to be substantially the same as the shapes and dimensions of the through-holes 321 and 322. As can be understood from FIGS. 17 and 18, the shape and dimensions of the −X-side head portion 343 are set to be the same as the shape and dimensions of the head portion 43 of the locking member 14 shown in FIGS. 3, 4, and 6. The shape of the +X-side head portion 344 is set to be a column shape having a cross-section with an oval shape whose X direction dimension is larger than that of the head portion 343.

In such a case, as shown in FIG. 19, when the user attaches the locking member 314 to the specific through-hole set 321S, 322S among the multiple through-hole sets 321, 322 formed in the second belt portion 312 in advance before mounting the wearable device 1 on the wrist 90, the user is prompted to attach the locking member 314 in an orientation in which the shapes of the neck portions 341 and 342 of the locking member 314 match the shapes of the through-hole set 321S, 322S, or in other words, in the original orientation. As a result, a case in which the locking member 314 is erroneously attached in an orientation of being rotated 180 degrees with respect to the original orientation (an attachment error) is prevented.

Modified Example 4

Another modified example of the above-described locking member 14 and second belt portion 12 will be described with reference to FIGS. 20, 21, and 22 (the locking member and second belt portion of the modified example are denoted by reference numerals 414 and 412 respectively). Note that in FIGS. 17, 18, and 19, elements corresponding to the elements in FIGS. 3, 4, and 6 are denoted by reference numerals that have been increased by 400 (thus, redundant description is omitted as appropriate).

Figure 22:
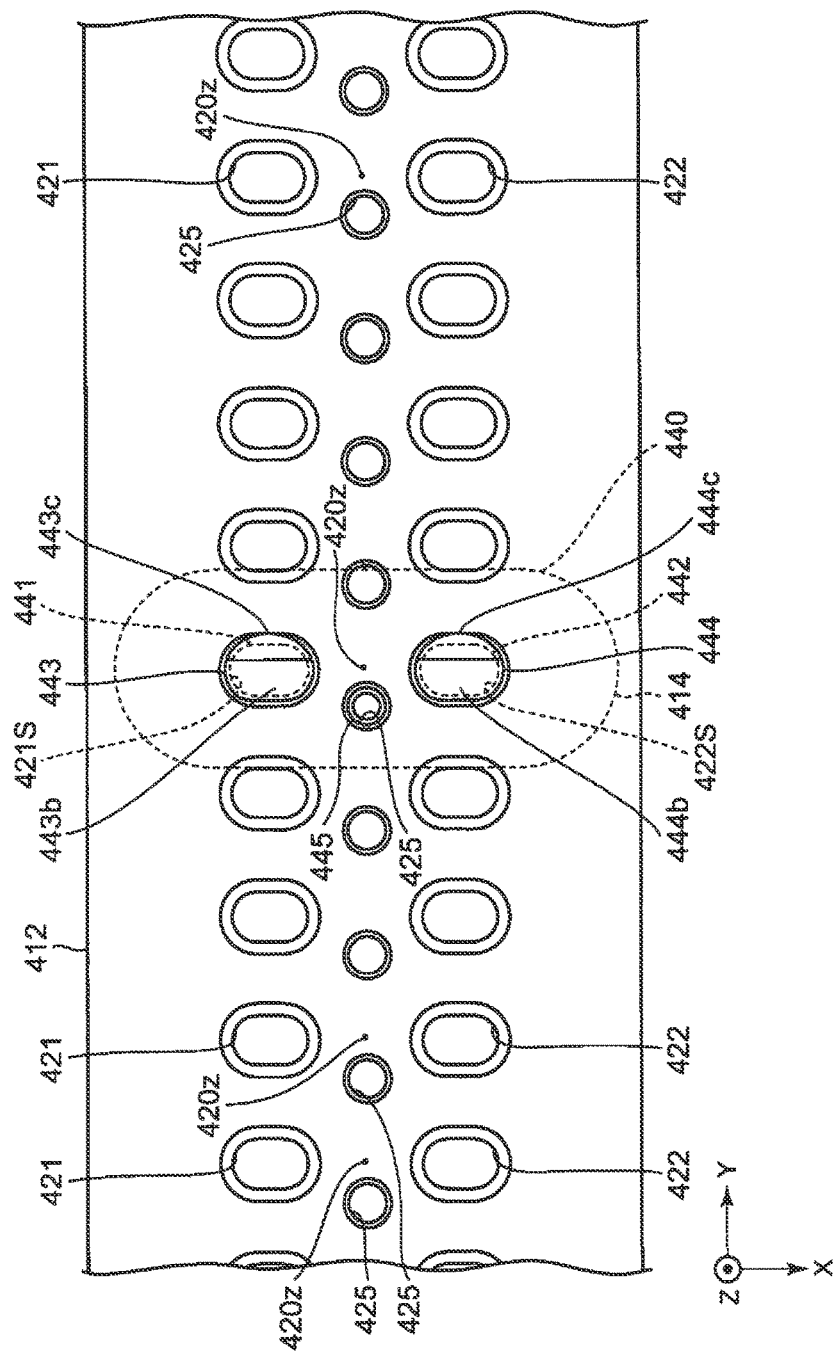
FIG. 22 is a planar layout diagram showing a state in which the locking member of Modified Example 4 is attached to a specific through-hole set of the second belt portion.

As shown in the planar layout in FIG. 22, through-hole sets 421, 422 are formed in alignment in the Y direction in the second belt portion 412, similarly to the second belt portion 12 shown in FIG. 6. The shapes and dimensions of the through-holes 421 and 422 that form the sets are set to be the same as the shapes and dimensions of the through-hole sets 21, 22 of the second belt portion 12 shown in FIG. 6. In this example, one more circular through-hole 425 is formed at each position of the through-hole sets 421, 422 aligned in the Y direction. The through-holes 425 function as recessed portions for determining the direction of the locking member 414 about the axis 420z that passes through the center of the corresponding through-hole set 421, 422 and is perpendicular to the second belt portion 412.

Figure 20:
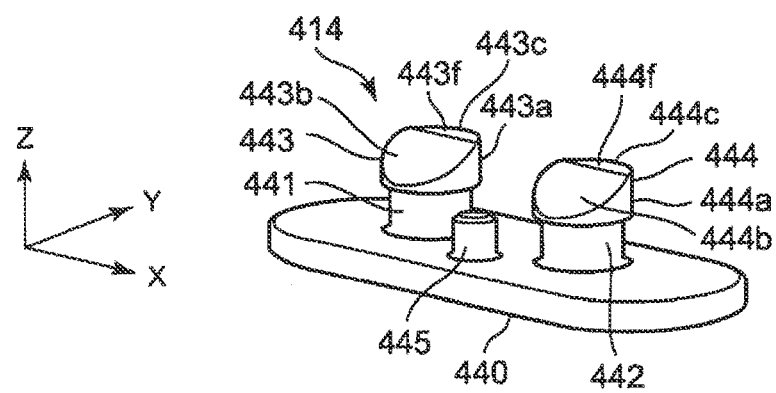
FIG. 20 is a perspective view showing a locking member of Modified Example 4.
Figure 21:
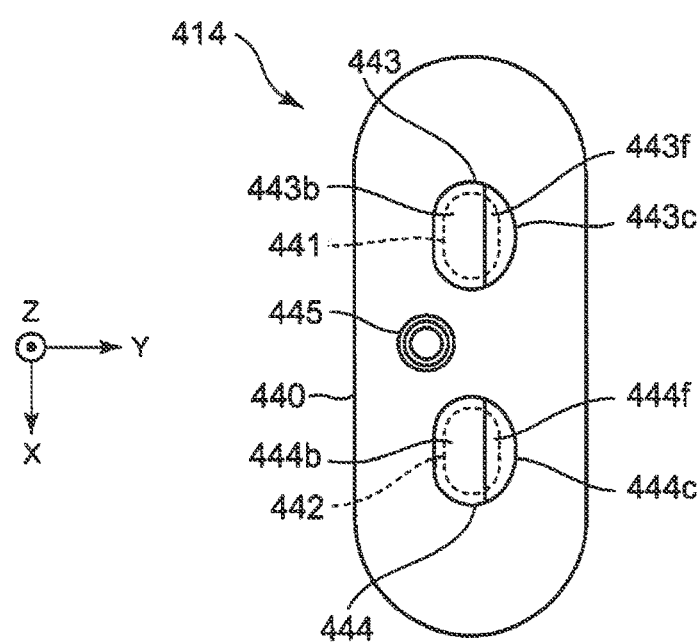
FIG. 21 is a plan view showing the locking member of Modified Example 4.

With the locking member 414, as can be understood in FIGS. 20 and 21, the shapes and dimensions of the neck portions 441 and 442 and the head portions 443 and 444 are set to be the same as the shapes and dimensions of the neck portions 41 and 42 and the head portions 43 and 44 of the locking member 14 shown in FIGS. 3, 4, and 6. In this example, an approximately cylindrical protrusion 445 that fits into the through-hole 425 of the second belt portion 412 only when the locking member 414 is oriented in a specific direction (shown in FIG. 22) about the axis 420z is provided on the base portion 440.

In such a case, as shown in FIG. 22, when the user attaches the locking member 414 to the specific through-hole set 421S, 422S among the multiple through-hole sets 421, 422 formed in the second belt portion 412 in advance before mounting the wearable device 1 on the wrist 90, the protrusion 445 of the base portion 440 fits into the through-hole 425 of the second belt portion 412 only when the locking member 414 is oriented in a specific direction (shown in FIG. 22) about the axis 420z. When the locking member 414 is oriented in another direction about the axis 420z, the protrusion 445 of the base portion 440 does not fit into the through-hole 425 of the second belt portion 412, and therefore the base portion 440 does not come into close contact with the rear surface of the second belt portion 412, and attachment cannot be reliably performed. Accordingly, a case is prevented in which the locking member 414 is attached in an orientation that is wrong with regard to its original orientation (an attachment error).

Note that the through-hole 425 need not necessarily penetrate through the second belt portion 412, and need only be recessed.

Modified Example 5

When removing the wearable device 1 from the wrist 90, it is desirable that the user is able to easily release the locking member 14 locked by the above-described side 33 of the ring 13.

Figure 23:
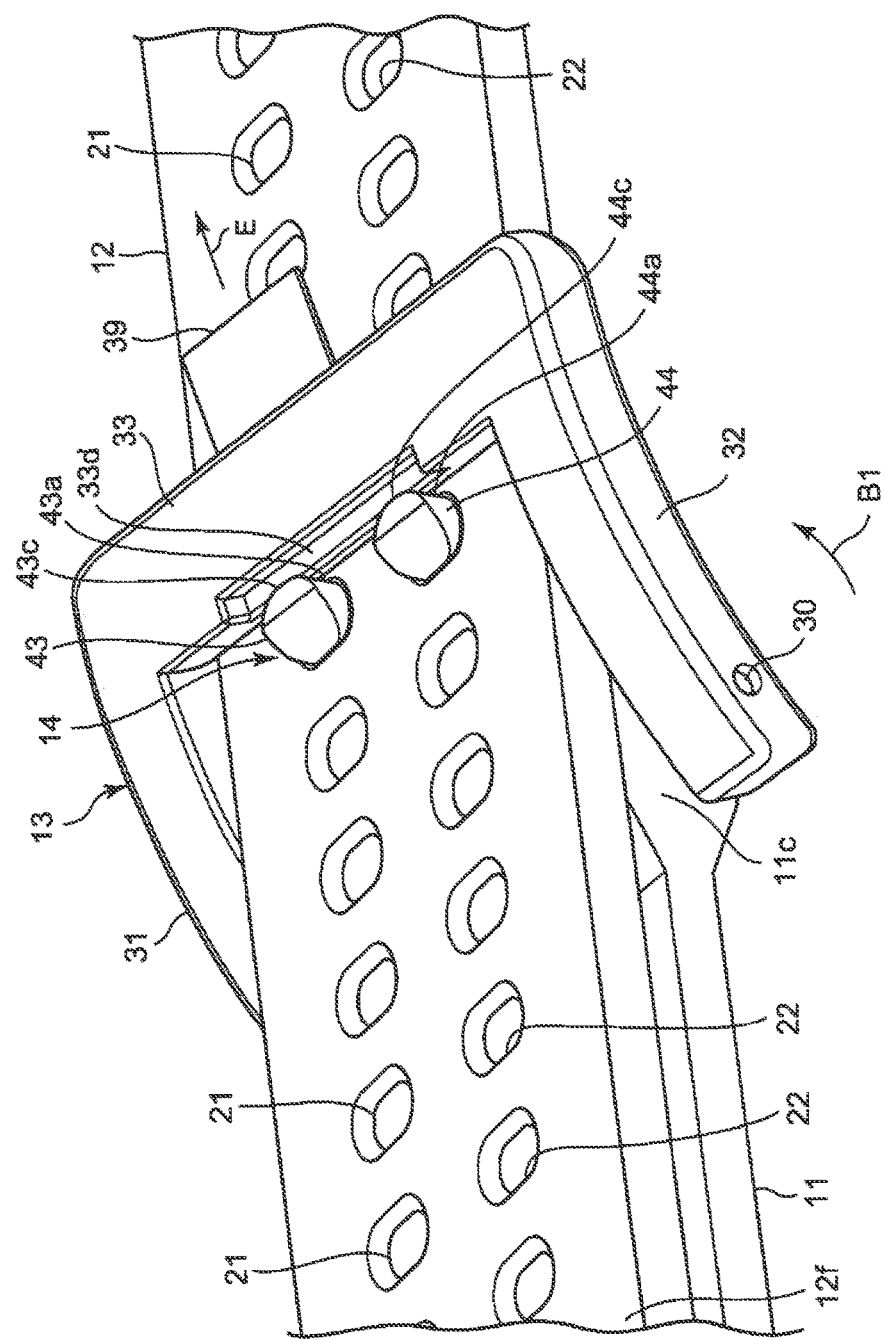
FIG. 23 is a perspective view showing a modified example (Modified Example 5) in which a side of the ring is provided with a tab serving as a removal mechanism.

FIG. 23 shows a modified example in which a tab 39 serving as a removal mechanism is provided on the side 33 of the ring 13. In this example, the tab 39 is composed of a band-shaped plastic material and is attached to the side 33 of the ring 13 so as to protrude outward (in the direction of moving away from the coupling rod 30). This kind of tab 39 can be provided relatively easily.

When the wearable device 1 is to be removed from the wrist 90, the user pinches the tab 39 with his or her fingers and pulls in the direction of arrow E in FIG. 23. Upon doing so, the first belt portion 11 extends slightly due to the pulling force, and the ring 13 moves slightly in the direction of the arrow E. Accordingly, the side 33 (edge portion 33d of the side 33) of the ring 13 and the head portions 43 and 44 of the locking member 14 are separated from each other. As a result, the user can rotate the ring 13 in the direction of arrow B1 and can easily release the locking member 14 locked by the ring 13.

This makes it possible for the user to easily remove the wearable device 1 from the wrist 90.

Modified Example 6

A modified example in which a removal mechanism 150 including a release button 151 is provided on the side 133 of the ring 113 corresponding to the above-described ring 13 will be described with reference to FIGS. 24, 25, and 26. Note that in FIGS. 24, 25, and 26, the same reference numerals are used for elements that are the same as above-described elements.

Figure 24:
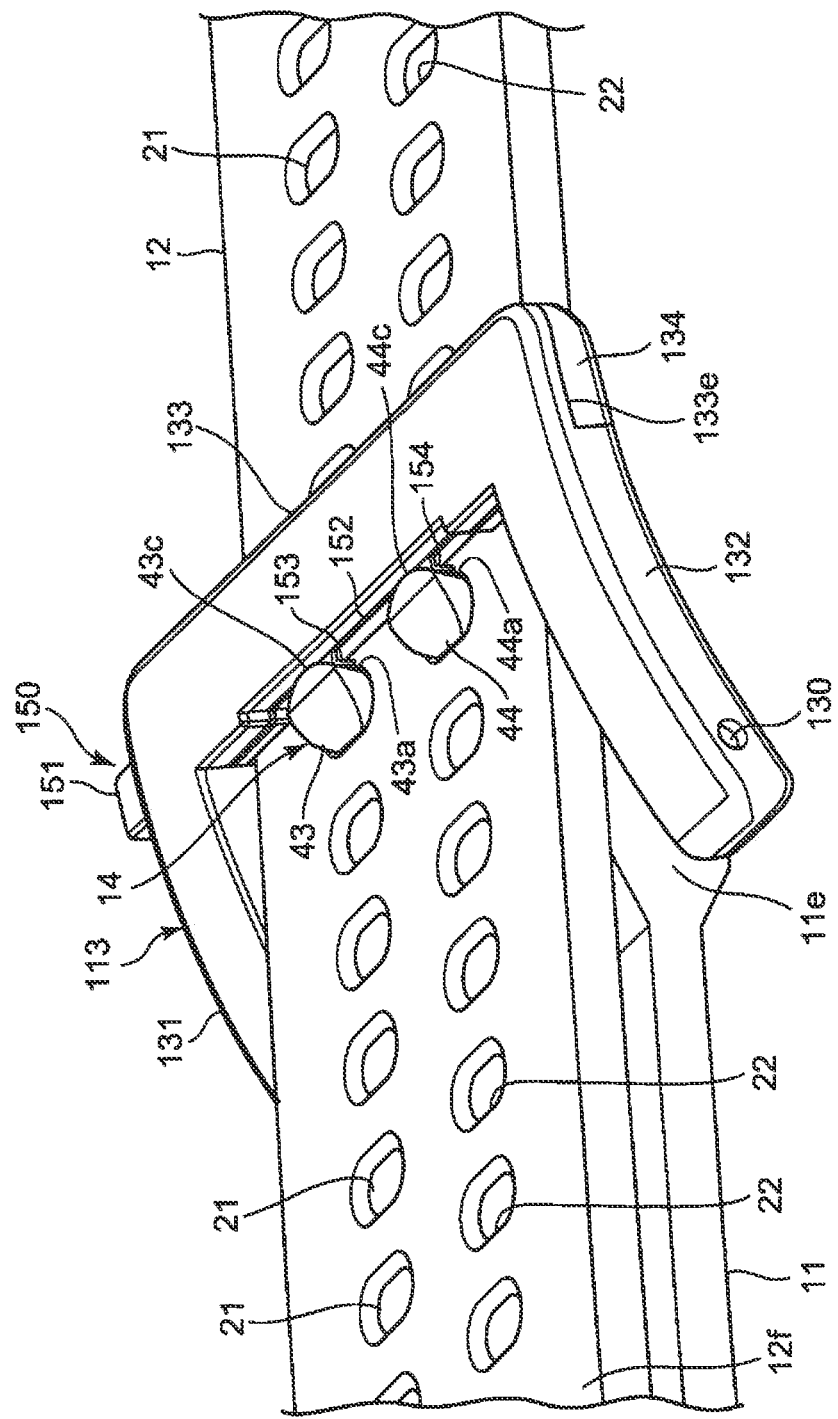
FIG. 24 is a perspective view showing a modified example (Modified Example 6) in which a side of the ring is provided with a removal mechanism including a release button.

In this example, as shown in FIG. 24, the ring 113 includes the coupling rod (known spring rod) 130 provided so as to penetrate through the end portion 11e of the first belt portion 11, and an approximately U-shaped member (the three sides of this U-shaped member being denoted by reference numerals 131, 132, and 133) attached rotatably to the coupling rod 130. The side (side corresponding to the side opposite to the coupling rod 130) 133 in the center of the U-shaped member is divided into upper and lower portions via an L-shaped borderline 133e (the lower portion of the side 133 being denoted by reference numeral 134), and includes the removal mechanism 150 in its interior.

Figure 25:
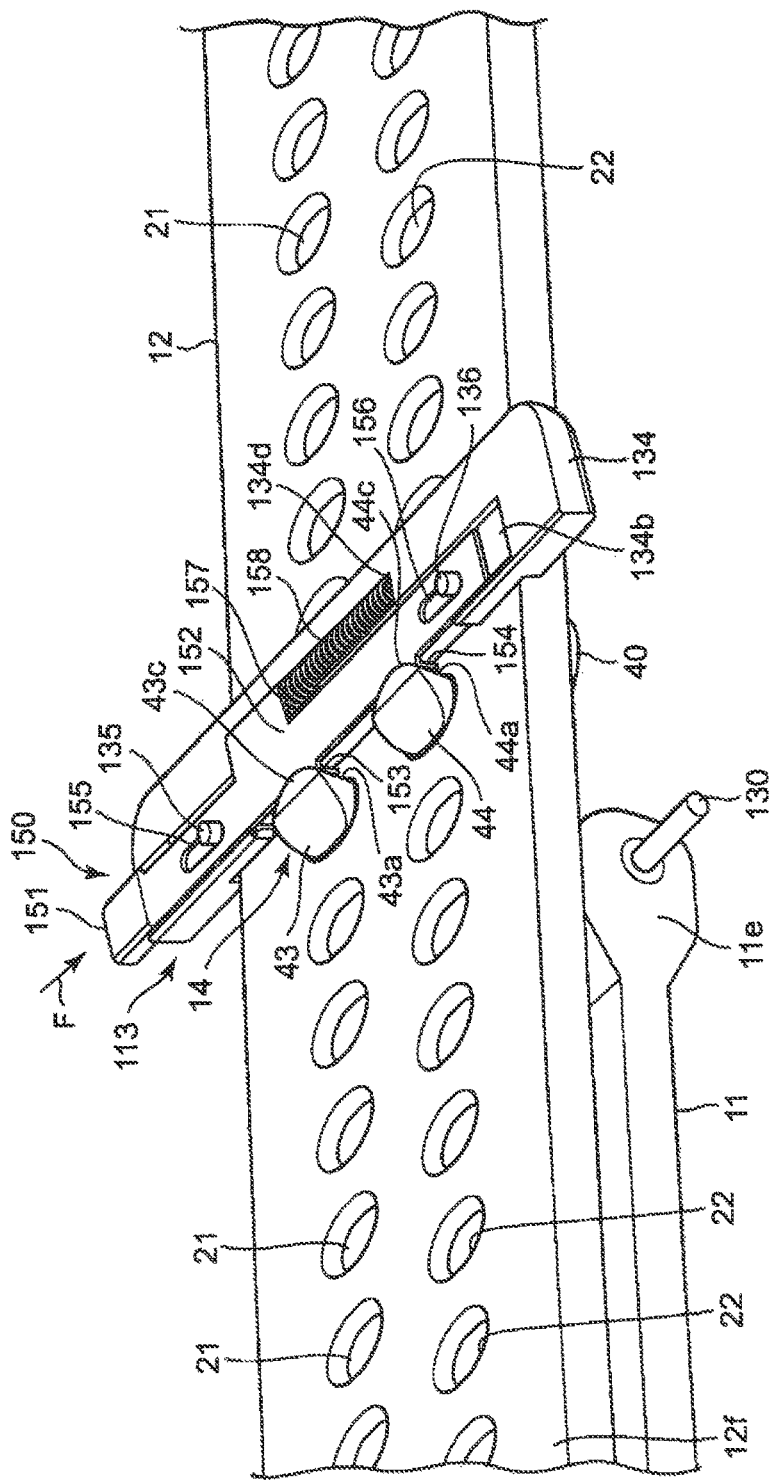
FIG. 25 is a perspective view showing a state in which the lower portion of the side in the center of the ring remains and the three sides forming a U-shaped member have been removed in FIG. 24.
Figure 26:
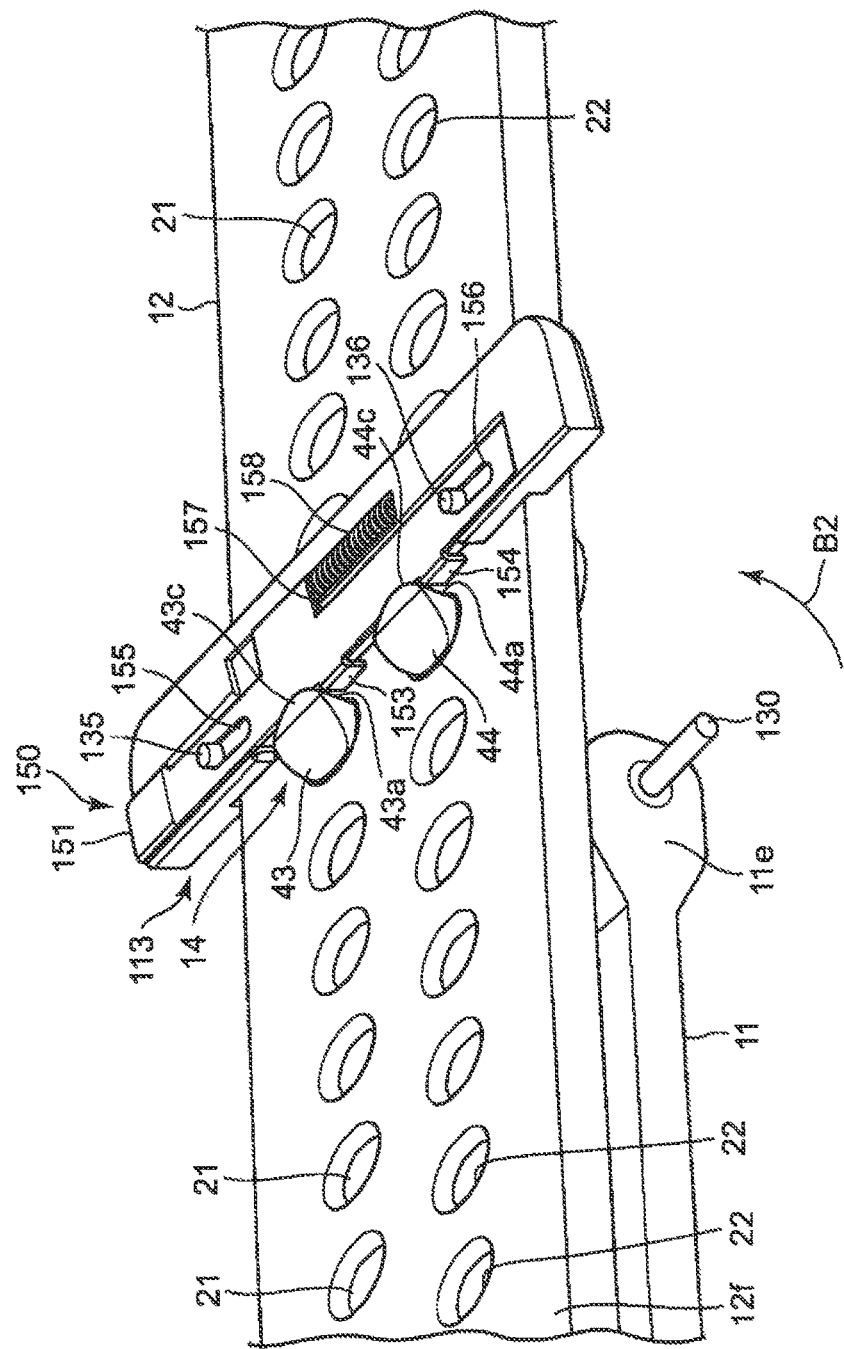
FIG. 26 is a perspective view showing a state in which the release button is pressed in FIG. 25.

In order to facilitate understanding, FIG. 25 shows a state in which the portion 134 of the side in the center remains and the three sides 131, 132, and 133 of the U-shaped member have been removed. The removal mechanism 150 includes a release button 151 that protrudes outward, and a slide plate 152 that is integral with the release button 151 and is accommodated so as to be able to slide frontward and rearward (in the X direction in FIG. 1) in the groove 134b of the lower portion 134 of the side in the center. The slide plate 152 has L-shaped claws 153 and 154 that come into contact with contact surfaces 43a and 43b of the head portions 43 and 44 of the locking member 14 on the side near the coupling rod 130. Also, the slide plate 152 has a pair of oval-shaped through-holes 155 and 156 that extend in the X direction on the far and near sides. The through-holes 155 and 156 fit over guide pins 135 and 136 that are provided so as to protrude from the groove 134b of the lower portion 134 of the side in the center. Also, the slide plate 152 has a receiving surface 157 for receiving a coil spring on the side far from the coupling rod 130. The coil spring 158 is provided in a contracted state between the receiving surface 157 and the opposing surface 134d on the lower portion 134 of the side in the center.

If no external force is applied to the release button 151, the slide plate 152 is in a state of being moved to the far side (−X side in FIG. 1) by the extending force of the coil spring 158. Thus, the head portions 43 and 44 of the locking member 14 are locked by the L-shaped claws 153 and 154. In this state, when the user presses the release button 151 in the direction indicated by arrow F in order to remove the wearable device 1 from the wrist 90, the slide plate 152 moves to the near side (+X side in FIG. 1) as shown in FIG. 26 against the extending force of the coil spring 158 while being guided by the guide pins 135 and 136 via the through-holes 155 and 156. Accordingly, the L-shaped claws 153 and 154 come off of the contact surfaces 43a and 43b of the head portions 43 and 44 of the locking member 14. As a result, the user can rotate the ring 113 in the direction of arrow B2 and can easily release the locking member 14 locked by the ring 113.

This makes it possible for the user to easily remove the wearable device 1 from the wrist 90.

Modified Example 7

Another embodiment in which a removal mechanism 250 including a release button 251 is provided on a side 233 of a ring 213 that corresponds to the above-described ring 13 will be described with reference to FIGS. 27 and 28. Note that in FIGS. 27 and 28, the same reference numerals are used for elements that are the same as above-described elements.

Figure 27:
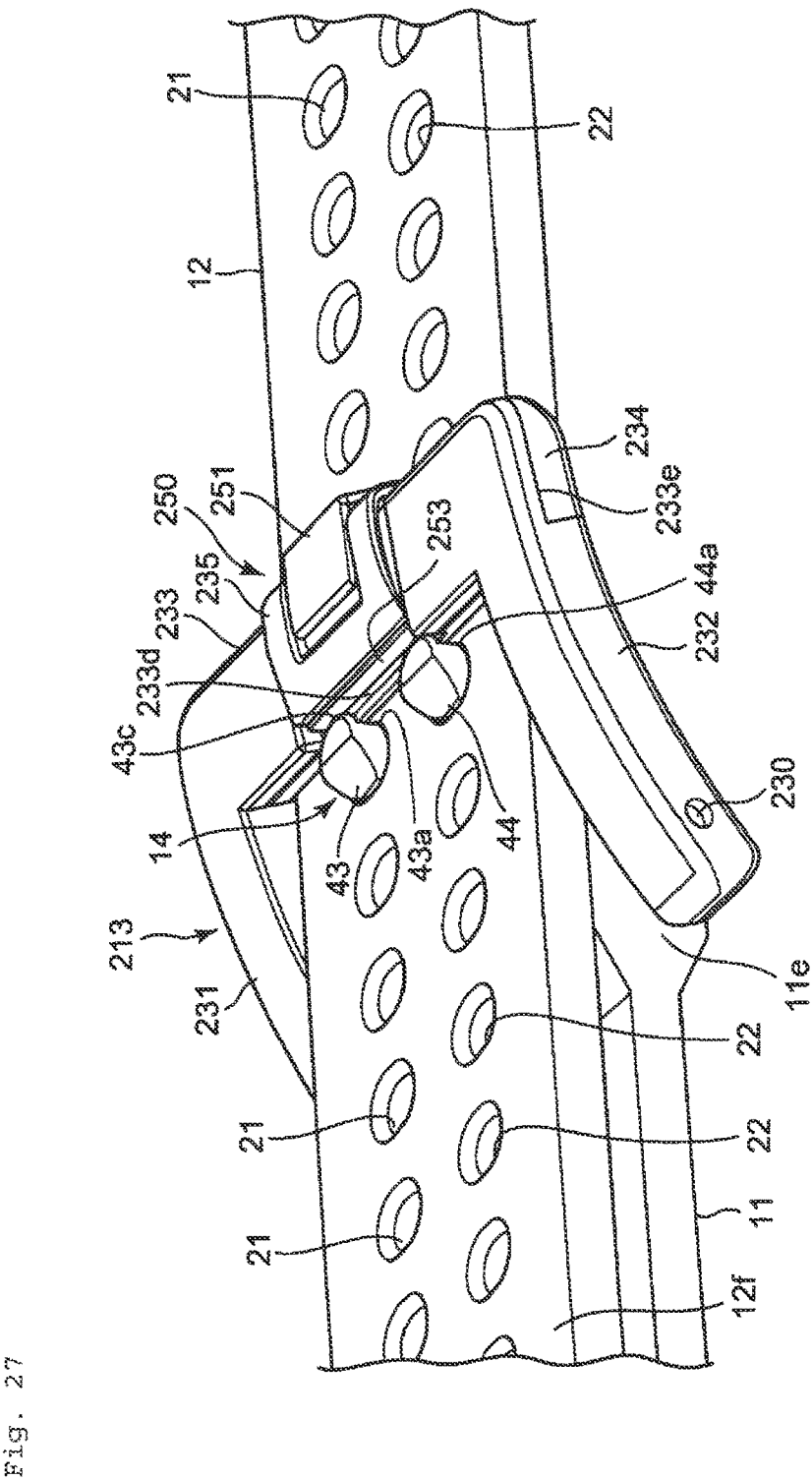
FIG. 27 is a perspective view showing another modified example (Modified Example 7) in which a side of the ring is provided with a removal mechanism including a release button.

In this example, as shown in FIG. 27, the ring 213 includes the coupling rod (known spring rod) 230 provided so as to penetrate through the end portion 11e of the first belt portion 11, and an approximately U-shaped member (the three sides of this U-shaped member being denoted by reference numerals 231, 232, and 233) attached rotatably to the coupling rod 230. The side (side corresponding to the side opposite to the coupling rod 230) 233 in the center of the U-shaped member is divided into upper and lower portions via an L-shaped borderline 233e (the lower portion of the side 233 being denoted by reference numeral 234), and includes the removal mechanism 250 in its interior. Note that a cover 235 of the removal mechanism 250 is attached integrally to the side 233 (upper portion) in the center.

Figure 28:
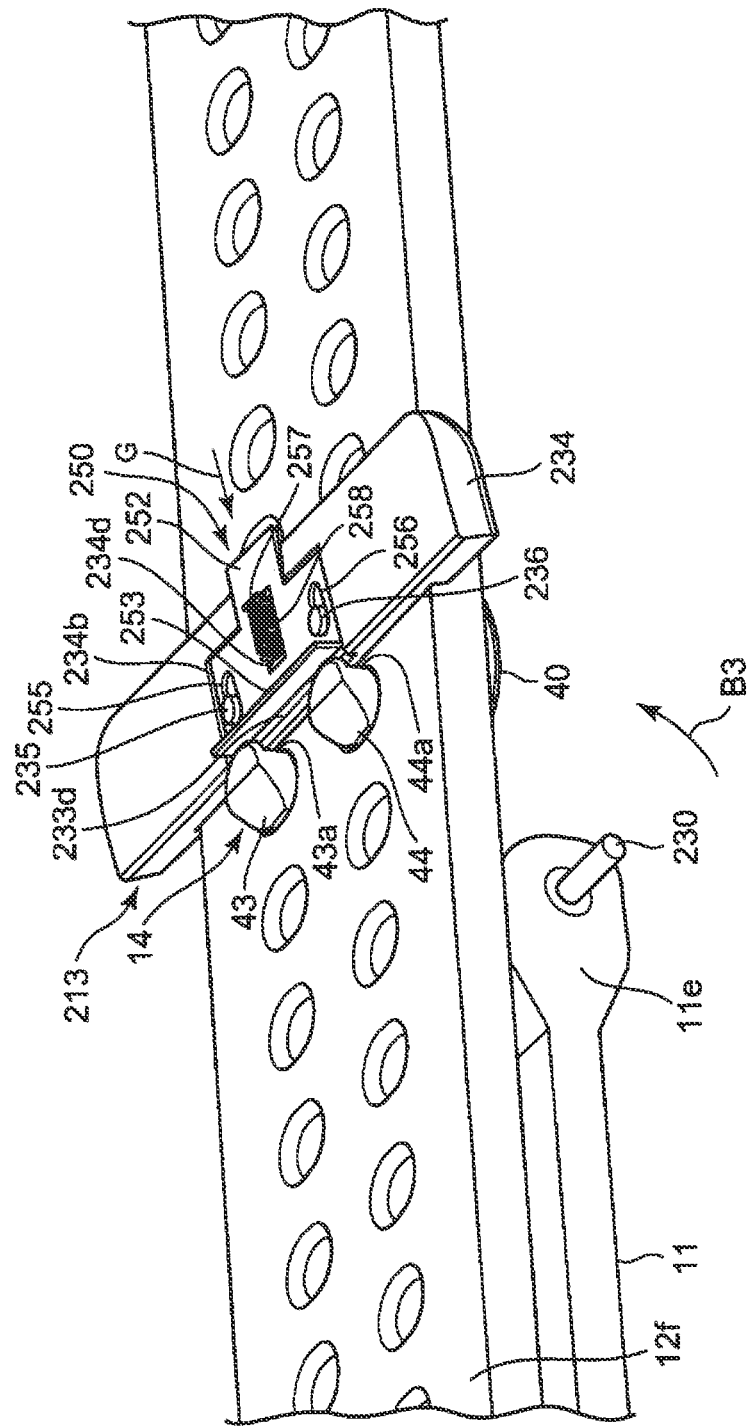
FIG. 28 is a perspective view showing a state in which the lower portion of the side in the center of the ring remains and the three sides forming a U-shaped member have been removed in FIG. 27.

In order to facilitate understanding, FIG. 28 shows a state in which the portion 234 of the side in the center remains and the three sides 231, 232, and 233 of the U-shaped member have been removed. The removal mechanism 250 includes a slide plate 252 that is integral with the release button 251 (FIG. 27) and is accommodated so as to be able to slide left and right (in the Y direction in FIG. 1) in the groove 234b of the lower portion 234 of the side. The slide plate 252 has a press surface 253 that comes into contact with brim portions 43c and 44c of the head portions 43 and 44 of the locking member 14 on a side near the coupling rod 230. Also, the slide plate 252 has a pair of oval-shaped through-holes 255 and 256 that extend in the Y direction on the far and near sides. The through-holes 255 and 256 fit over guide pins 235 and 236 that are provided so as to protrude from the groove 234b of the lower portion 234 of the side in the center. Also, the slide plate 252 has a receiving surface 257 for receiving a coil spring on a side far from the coupling rod 230. The coil spring 258 is provided in a contracted state between the receiving surface 257 and the opposing surface 234d on the lower portion 234 of the side in the center.

If no external force is applied to the release button 251, the slide plate 252 is in a state of being moved to the right side (+Y side in FIG. 1) by the extending force of the coil spring 258. Thus, the head portions 43 and 44 of the locking member 14 are locked by the thin edge portion 233d of the lower portion 234 of the side in the center. In this state, when the user presses the release button 251 in the direction indicated by arrow G in order to remove the wearable device 1 from the wrist 90, the slide plate 252 moves to the left side (−Y side in FIG. 1) against the extending force of the coil spring 258 while being guided by the guide pins 235 and 236 via the through-holes 255 and 256. Accordingly, the press surface 253 presses the brim portions 43c and 44c of the head portions 43 and 44 of the locking member 14 to the left side. Thus, the head portions 43 and 44 of the locking member 14 come off of the thin edge portion 233d of the lower portion 234 of the side in the center. As a result, the user can rotate the ring 213 in the direction of arrow B3 and can easily release the locking member 14 locked by the ring 213.

This makes it possible for the user to easily remove the wearable device 1 from the wrist 90.

Modified Example 8

Figure 29:
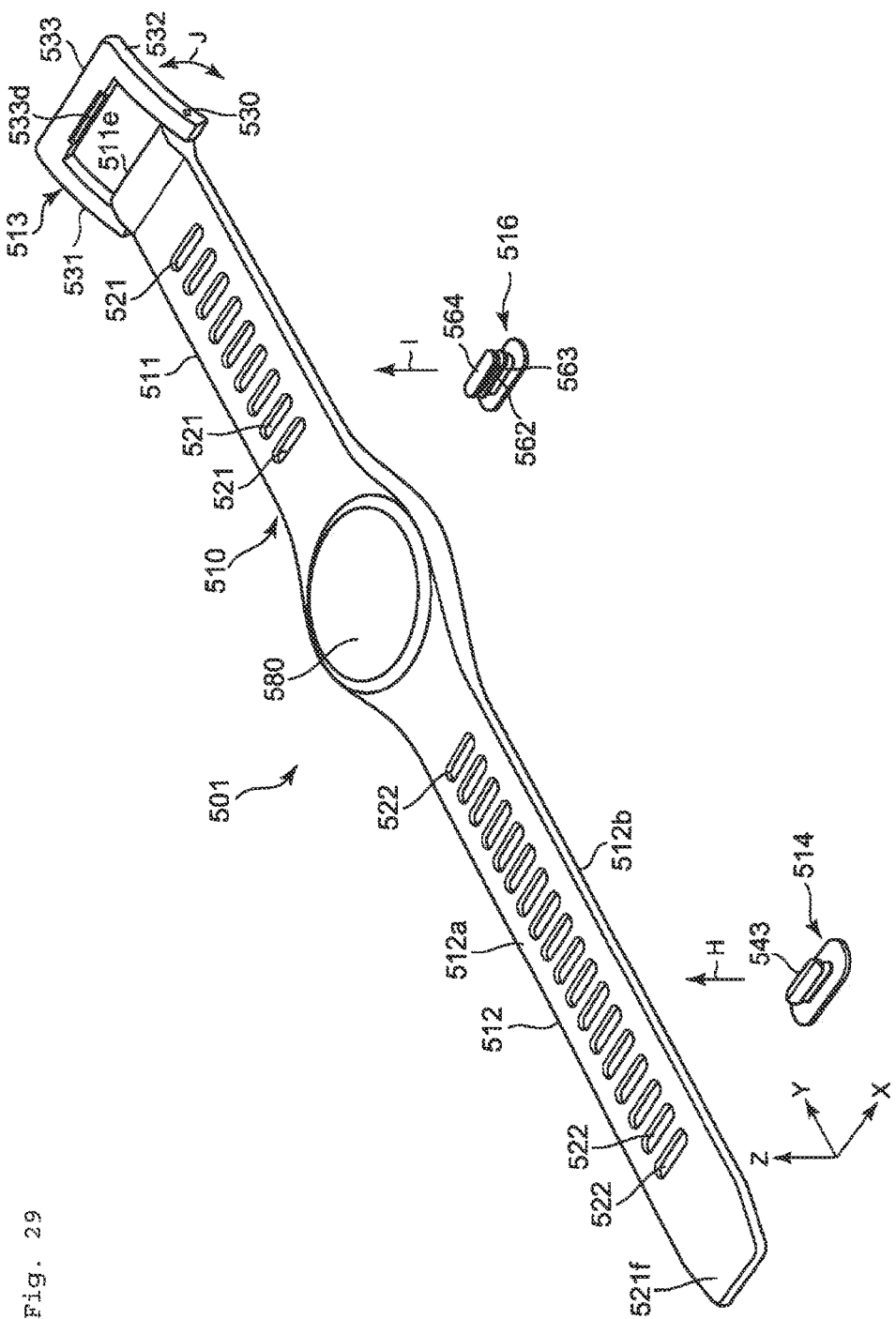
FIG. 29 is a diagram showing a perspective view of a wearable device according to a modified example (Modified Example 8), to which the belt of the present invention has been applied.

FIG. 29 shows a perspective view of a wearable device 501 according to a modified example. The wearable device 501 includes a belt (hereinafter referred to as a "belt main body") that extends in the form of a long, narrow band, and a device 580 to be attached to a wrist of a body using the belt main body 510. In this example, the device 580 includes the functions of an activity level meter and a pulse meter. Note that in FIG. 29 (and later-described FIGS. 30 to 33), elements that correspond to the elements in FIG. 1 are denoted by reference numerals increased by 500 (thus, redundant description is omitted as appropriate).

In this example, the belt main body 510 is composed of flexible silicone resin (a modulus that expresses elasticity being 20 to 65 [MPa]), and includes a first belt portion 511 that corresponds to a side (+Y side) of an end in the Y direction, which serves as the lengthwise direction, and a second belt portion 512 that corresponds to the side (−Y side) opposite to the first belt portion 511 in the Y direction. The device 580 is integrally built-in between the first belt portion 511 and the second belt portion 512.

An approximately rectangular ring 513 serving as the frame-shaped body is attached to an end portion 511e on the side of the first belt portion 511 that is far from the device 580 (i.e., the +Y side). The ring 513 is the same as the above-described ring 13 and can rotate as indicated by double-arrow J.

In this example, through-holes 522 are formed in alignment along the Y direction in the second belt portion 512. Through-holes 521 are formed in alignment along the Y direction in the first belt portion 511 as well. In this example, the through-holes 521 and 522 are formed to have the same oval shape as each other.

Figure 31:
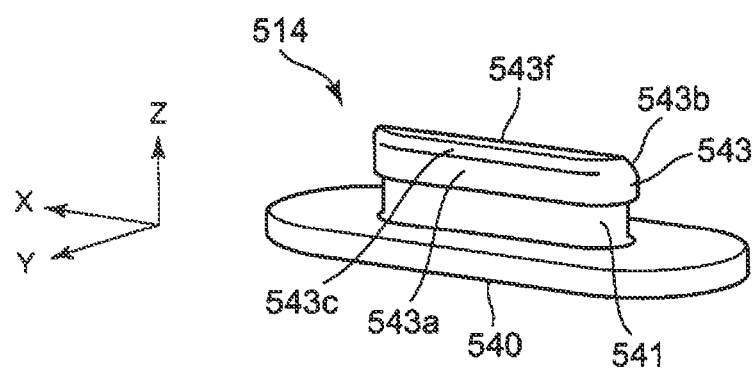
FIG. 31 is a perspective view showing the locking member shown in FIG. 30.

The locking member 514 shown in FIG. 29 is attached to the through-hole 522 of the second belt portion 512. As shown in FIG. 31 (perspective view), the locking member 514 has a mode in which the neck portions 41 and 42 of the above-described locking member 14 are combined into one and the head portions 43 and 44 are combined into one. Specifically, the locking member 514 has a base portion 540 having a mode of being a flat plane with an oval shape, a neck portion 541 that is continuous with the base portion 540 and has substantially the same shape and dimensions as the shape and dimensions of the through-hole 522 of the second belt portion 512, and a head portion 543 that has a mode of being an oval-shaped column having dimensions larger than the dimensions of the through-hole 522. On the upper side (+Z side), the head portion 543 has, in the following order: an inclined surface 543b that is inclined in an orientation of being located gradually farther away from the base portion 540 as the +Y side is approached from the −Y side, a flat surface 543f that is continuous with the inclined surface 543b and is parallel with the base portion 540, and a brim portion 543c that is continuous with the flat surface 543f and protrudes toward the +Y side from the side surface (surface of contact with side 533 of the ring 513) 543a on the front side (+Y side) in FIG. 29.

Figure 32:
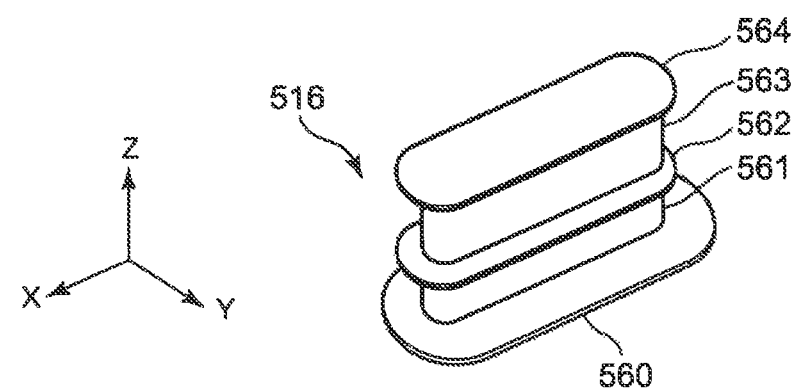
FIG. 32 is a perspective view showing the fixing member shown in FIG. 30.

A fixing member 516 shown in FIG. 29 is attached to the through-hole 521 of the first belt portion 511. As shown in FIG. 32 (perspective view), the fixing member 516 has, in the following order: a base portion 560 having a mode of being an oval-shaped flat plate, a first neck portion 561 having substantially the same shape and dimension as the shape and dimension of the through-hole 521 of the first belt portion 511, a flange portion 562 that protrudes in an oval shape about the upper edge of the first neck portion 561, a second neck portion 563 that is continuous with the flange portion 562 and has substantially the same shape and dimension as the shape and dimension of the through-hole 522 of the second belt portion 512, and a peak portion 564 having a mode of being an oval-shaped flat plate formed on the upper end of the second neck portion 563.

Figure 30:
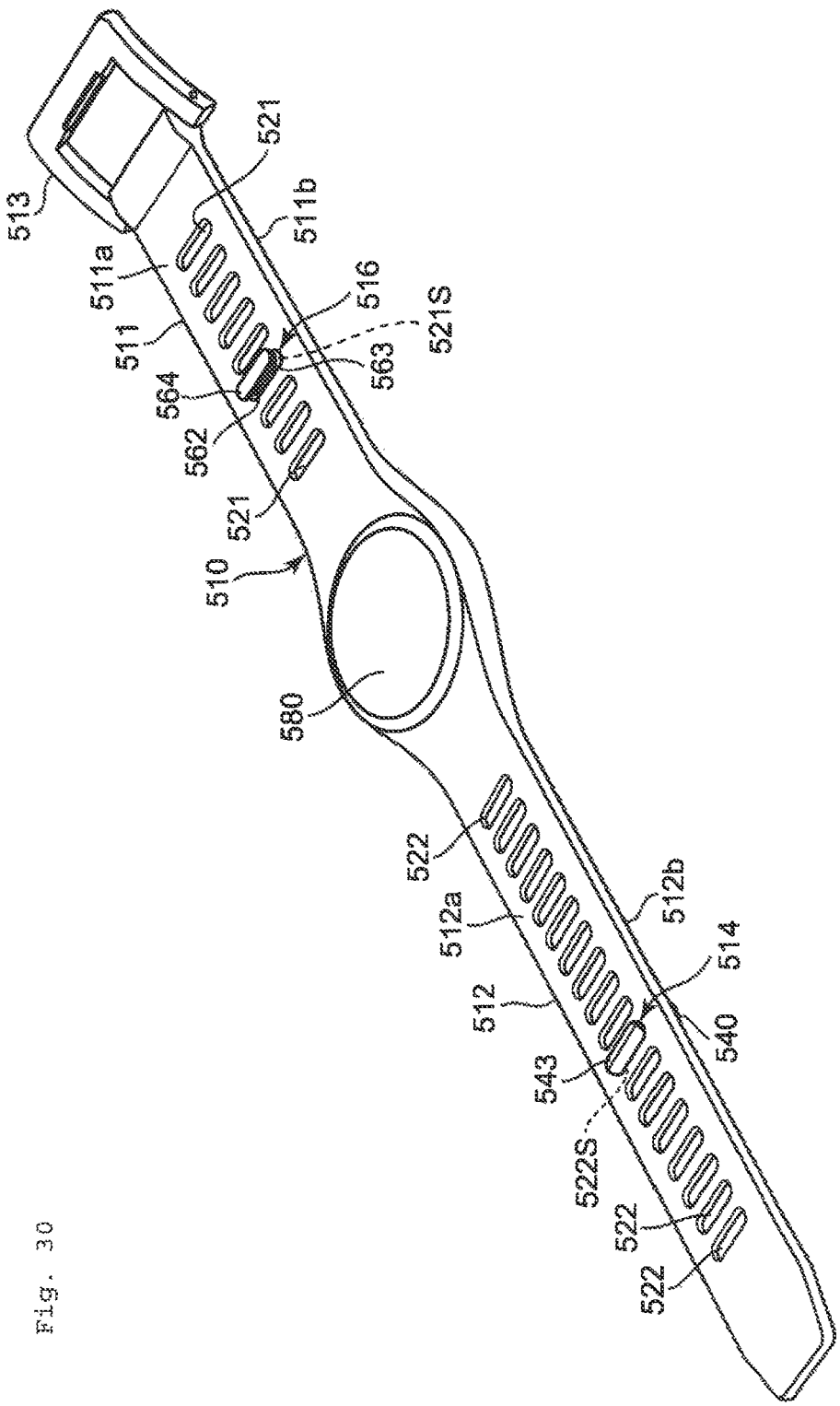
FIG. 30 is a perspective view showing a state in which a locking member is attached to a specific through-hole of the second belt portion of the wearable device shown in FIG. 29 and a fixing member is attached to a specific through-hole of the first belt portion.

When the wearable device 501 is to be mounted on the wrist 90 serving as the target object, as shown in FIG. 30, the user attaches the locking member 514 in advance to a specific through-hole (indicated by reference numeral 522S) among the multiple through-holes 522 formed in the second belt portion 512 of the belt main body 510, such that the head portion 543 protrudes from the front surface of the second belt portion 512.

For example, as indicated by arrow H in FIG. 29, the user pushes the head portion 543 of the locking member 514 through the through-hole 522S from the rear surface 512b side of the second belt portion 512, whereby the locking member 514 is easily attached to the through-hole 522S, similarly to the above-described locking member 14. When the locking member 514 is attached to the through-hole 522S, the inclined surface 543b of the head portion 543 of the locking member 514 enters a state of being located gradually farther away from the front surface 512a of the second belt portion 512 as the first belt portion 511 is approached from the leading end 512f of the second belt portion 512 in the Y direction (forward-tapered state).

In addition to that, the user attaches the fixing member 516 to a specific through-hole (indicated by reference numeral 521S) among the multiple through-holes 521 formed in the first belt portion 511 of the belt main body 510, such that the peak portion 564, the second neck portion 563, and the flange portion 562 protrude from the front surface 511a of the first belt portion 511.

For example, as indicated by arrow 1 in FIG. 29, the user pushes the peak portion 564, the flange portion 562, and the second neck portion 563 of the fixing member 516 through the through-hole 521S from the read surface 511b side of the first belt portion 511, whereby the fixing member 516 is easily attached to the through-hole 521S. The mode of attaching the fixing member 516 is a mode in which the base portion 560 comes into contact with the rear surface 511b of the first belt portion 511, the first neck portion 561 extends through the through-hole 521S to the front surface 511a of the first belt portion 511, and the peak portion 564, the second neck portion 563, and the flange portion 562 protrude outward from the front surface 512a.

When actually mounting the wearable device 501 on the wrist 90, mounting is performed using a procedure that is the same as that described above with reference to FIGS. 7 to 9.

Here, the inclined surface 543b of the head portion 543 of the locking member 514 is in the forward-tapered state, and therefore the head portion 543 of the locking member 514 easily goes past the side 533 of the ring 513. Accordingly, the wearable device 501 is easily mounted on the wrist 90, similarly to the above-described example. In the state in which the belt main body 510 is mounted on the wrist 90, the side 533 of the ring 513 locks the head portion 543 of the locking member 514.

Figure 33:
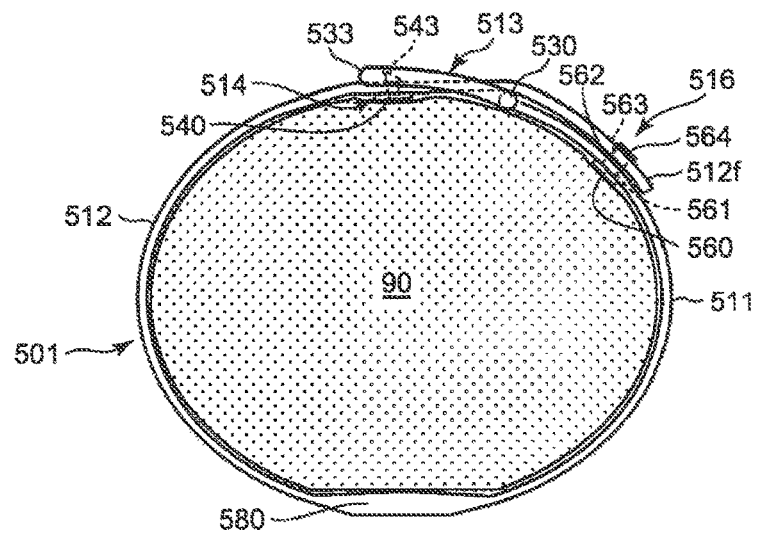
FIG. 33 is a diagram showing a state in which the vicinity of the leading end of the second belt portion is fixed to a corresponding portion of the first belt portion by the fixing member.

Furthermore, in this example, as shown in FIG. 33, the portion of the second belt portion 512 that is past the side 533 of the ring 513 (includes leading end 512f) is fixed to the corresponding portion of the first belt portion 511 by the fixing member 516. Specifically, the second neck portion 563 is fit into the corresponding through-hole 522 near the leading end 512f of the second belt portion 512 by pressing the peak portion 564 of the fixing member 516 that protrudes outward from the front surface 511a of the first belt portion 511.

In such a case, the wearable device 501 is reliably mounted on the wrist 90. Also, it is possible to prevent a case in which the portion of the second belt portion 512 past the side 533 of the ring 513 dangles and gets in the way or tarnishes the appearance when the wrist 90 moves.

As the specific through-hole 521S to which the fixing member 516 is to be fixed in the above-described first belt portion 511, it is desirable to select a through-hole set that will overlap with the vicinity of the leading end 512f of the second belt portion 512 when the belt main body 510 is wrapped around the wrist 90 with a certain tensile force (encompasses the case where the tensile force is substantially zero) that is suitable for the function of the device 580, for example. Accordingly, the vicinity of the leading end 512f of the second belt portion 512 is attached precisely to the fixing member 516.

Note that instead of the fixing member 516, it is also possible to provide a fixed strap that wraps around the first belt portion 511 and a free strap, and to fix the leading end 512f of the second belt portion 512 to the first belt portion 511 using the fixed strap and free strap.

Alternatively, magnets may be provided at the vicinity of the leading end 512f of the second belt portion 512 and a corresponding position on the first belt portion 511, and the leading end 512f of the second belt portion 512 may be fixed to the first belt portion 511 using the attraction between the magnets.

Modified Example 9

Figure 34:
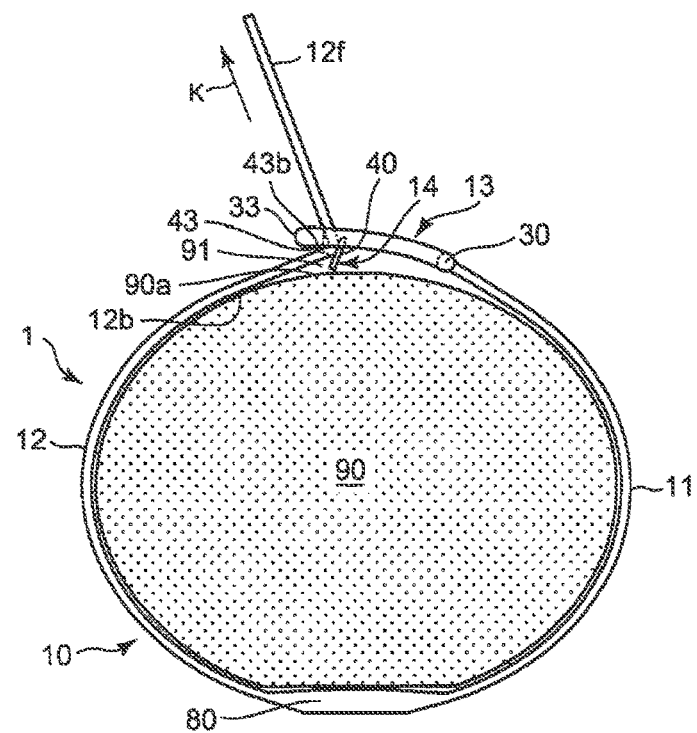
FIG. 34 is a diagram illustrating the problem of tissue (flesh) of a wrist surface being caught between the rear surface of the second belt portion and the base portion of the locking member.

If the above-described locking member 14 (see FIGS. 3 to 5) is used, in the case of actually mounting the wearable device 1 on the wrist 90, when the user pulls the leading end 12f of the second belt portion 12 such that the portion of the second belt portion 12 to which the locking member 14 is attached bends with a relatively small curvature radius in the direction indicated by arrow K in FIG. 34, for example, a gap 91 that is open toward the wrist 90 appears between the rear surface 12b of the second belt portion 12 and the base portion 40 of the locking member 14. In this state, when the user releases the leading end 12f of the second belt portion 12, the gap 91 starts to close, and there is a possibility that tissue (flesh) of the wrist surface 90a will be caught between the rear surface 12b of the second belt portion 12 and the base portion 40 of the locking member 14.

Figure 5:
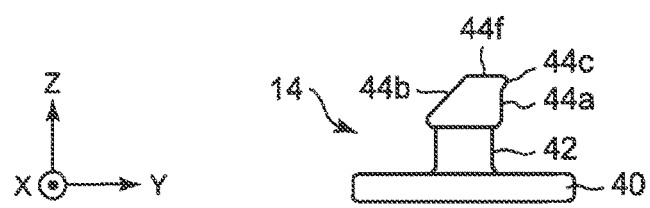
FIG. 5 is a side view showing the locking member.
Figure 35:
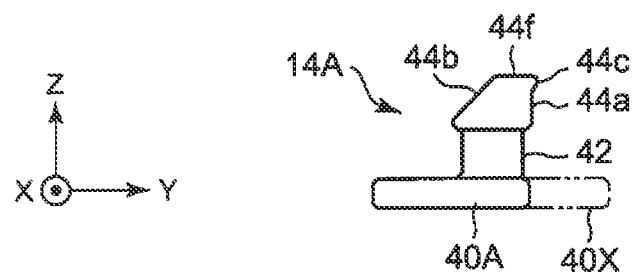
FIG. 35 is a side view showing a modified example (Modified Example 9) of a locking member, in which a countermeasure against the problem has been carried out.

In correspondence to FIG. 5, FIG. 35 shows a modified example of the locking member 14, in which a countermeasure against this situation has been carried out (the locking member of the modified example being indicated by reference numeral 14A). Note that in FIG. 35, elements that are the same as the elements in FIG. 5 are denoted by the same reference numerals (thus, redundant description is omitted as appropriate).

The base portion 40A of the locking member 14A exists only in the region corresponding to the −Y side from the neck portion 42 (and 41) along the Y direction, and does not exist in the region corresponding to the +Y side with respect to the neck portion 42 (and 41) (a portion 40X indicated by the two-dot chain line in FIG. 35 is omitted compared to the base portion 40 of the locking member 14). As a result, when the locking member 14 is attached to the through-hole set 21, 22 of the second belt portion 12, the base portion 40 of the locking member 14 exists only in the region corresponding to the leading end 12f side of the second belt portion 12 from the neck portions 41 and 42 in the Y direction, and does not exist in the region corresponding to the opposite side.

Accordingly, the gap 91 shown in FIG. 34 no longer appears. Accordingly, when the wearable device 1 is to be mounted on the wrist 90, it is possible to avoid an inconvenience in which tissue (flesh) of the wrist surface 90a is caught between the rear surface 12b of the second belt portion 12 and the base portion 40 of the locking member 14.

Modified Example 10

As described above, the tensile force of the belt main body 10 is set in the state in which the wearable device 1 (and 501) is mounted on the wrist 90. It is desirable that the tensile force is observable.

Figure 36:
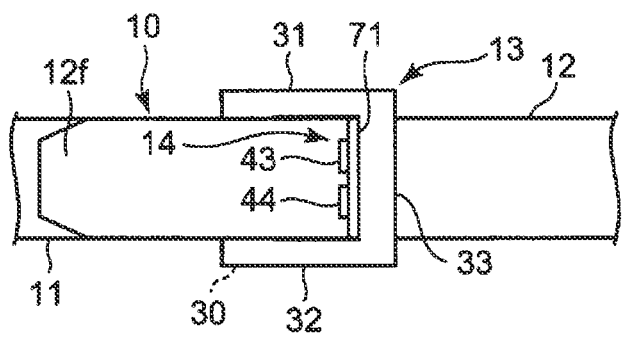
FIG. 36 is a diagram showing a modified example (Modified Example 10) in which the tensile force of a belt main body has been made observable.

FIG. 36 shows a modified example in which the tensile force of the belt main body 10 has been made observable.

In this example, a pressure sensor 71 serving as a detection unit is attached to the inner edge of the side 33 in the center of the ring 13. In the state in which the wearable device 1 is mounted on the wrist 90, the force between the first belt portion 11 and the second belt portion 12, or in other words, the tensile force of the belt main body 10 is applied to the pressure sensor 71 via the side 33 in the center of the ring 13 and the head portions 43 and 44 of the locking member 14.

As the pressure sensor 71, it is possible to use a pressure-sensitive conductive elastomer sensor (registered trademark "Inastomer") manufactured by Inaba Rubber Corporation, for example. The pressure sensor 71 includes a structure in which conducting particles are dispersed in elastomer, which is an insulator, and the electrical resistance of the overall sensor changes due to the internal conducting particles coming into contact with each other when pressure is applied. If the device 80 detects a change in the electrical resistance of the pressure sensor 71 as a pressure signal, the tensile force of the belt main body 10 can be observed.

Accordingly, the user can be made aware of the tensile force of the belt main body 10, and can check that the wearable device 1 is suitably mounted on the wrist 90.

Modified Example 11

Figure 37:
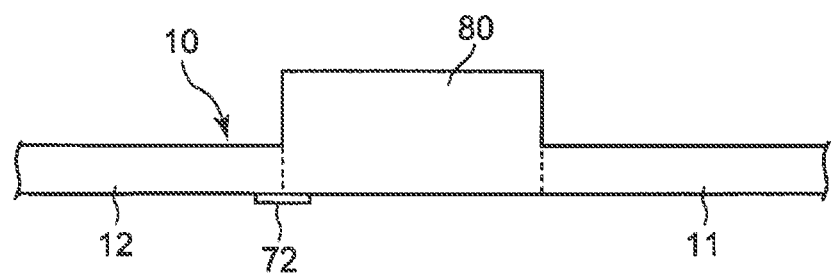
FIG. 37 is a diagram showing another modified example (Modified Example 11) in which the tensile force of the belt main body has been made observable.

FIG. 37 shows another modified example in which the tensile force of the belt main body 10 has been made observable.

In this example, a pressure sensor 72 serving as the detection unit is attached so as to span between the device 80 and the second belt portion 12. In the state in which the wearable device 1 is mounted on the wrist 90, the force between the device 80 and the second belt portion 12, or in other words, the tensile force of the belt main body 10 is applied to the pressure sensor 72.

As the pressure sensor 72, it is possible to use a foil strain gauge for plastic (product number KFP), which is manufactured by Kyowa Electronic Instruments Co., Ltd. The pressure sensor 72 extends (contracts) when tensile force (or contracting force) is applied from the outside, and the resistance thereof changes. If the device 80 detects a change in the electrical resistance of the pressure sensor 72 as a pressure signal, the tensile force of the belt main body 10 can be observed.

Accordingly, the user can be made aware of the tensile force of the belt main body 10, and can check that the wearable device 1 is suitably mounted on the wrist 90.

Modified Example 12

The locking member 14 shown in FIGS. 3 to 5, for example, has the neck portions 41 and 42 and the head portions 43 and 44 aligned in the X direction. However, there is no limitation to this.

Figure 38:
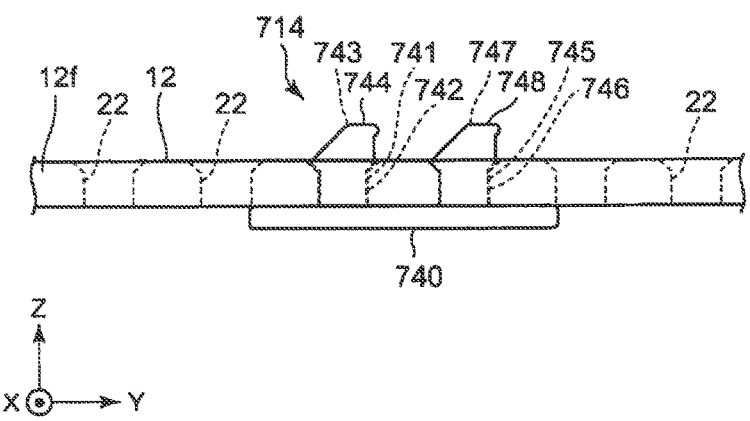
FIG. 38 is a diagram showing a modified example (Modified Example 12) in which the locking member is provided with four neck portions and four head portions corresponding thereto.

For example, the locking member (indicated overall by reference numeral 714) shown in FIG. 38 has a total of four neck portions 741, 742, 745, and 746, and a total of four head portions 743, 744, 747, and 748, which correspond to the neck portions, in alignment not only in the X direction but also in the Y direction, on the base portion 740. Note that in FIG. 38, the neck portions 741 and 745 and the head portions 743 and 747 corresponding thereto are arranged on the far side (−X side), and the neck portions 742 and 746 and the head portions 744 and 748 corresponding thereto are arranged on the near side (+X side).

The individual shapes of the neck portions 741, 742, 745, and 746, and the head portions 743, 744, 747, and 748 are set to be the same as the shapes of the neck portion 41 (and 42) and the head portion 43 (and 44) of the locking member 14.

Also, the distances in the X direction between the neck portions 741 and 742 and between the neck portions 745 and 746 are set to be the same as the distance in the X direction between the through-hole 21 and the through-hole 22, which form a set in the second belt portion 12. The distances in the Y direction between the neck portions 741 and 745 and between the neck portions 742 and 746 are set to be the same as the distance in the Y direction between a through-hole set 21, 22 of the second belt portion 12 and a through-hole set 21, 22 adjacent thereto.

As shown in FIG. 38, before the wearable device 1 is mounted on the wrist 90, the locking member 714 is attached to the second belt portion 12 in advance so as to span between two sets of through-hole sets that are adjacent to each other among the multiple through-hole sets 21, 22 formed in alignment in the Y direction.

In such a case, when the wearable device 1 is actually mounted on the wrist 90, the user can select a head portion of the locking member 714 that is to be locked with the side 33 of the ring 13 between the head portion set 743, 744 aligned in the X direction and the head portion set 747, 748 aligned in the X direction. For example, when the user wishes to perform mounting such that the tensile force of the belt main body 10 is relatively smaller, the head portion set 743, 744 on the side near the leading end 12f of the second belt portion 12 can be selected, and when the user wishes to perform mounting such that the tensile force of the belt main body 10 is relatively large, the head portion set 747, 748 on the side far from the leading end 12f of the second belt portion 12 can be selected. Accordingly, the user can suitably set the tensile force of the belt main body 10.

Modified Example 13

Figure 39:
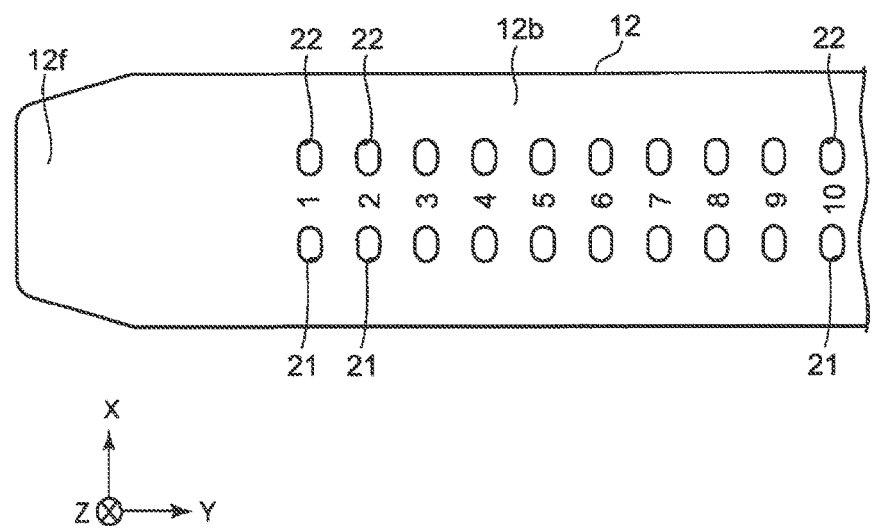
FIG. 39 is a diagram showing a modified example (Modified Example 13) in which numbers for specifying through-hole sets have been added to the rear surface of the second belt portion.

As shown in FIG. 39, it is desirable to add numbers "1", "2", "3", . . . for specifying the through-hole sets 21, 22; 21, 22; 21, 22 . . . aligned in the Y direction to the rear surface 12b of the second belt portion 12.

In such a case, it is easier for the user to select the through-hole set to which the locking member 14 is to be attached among the through-hole sets 21, 22; 21, 22; 21, 22 . . . of the second belt portion 12.

Note that it is naturally the case that English letters "A", "B", "C", . . . , other signs, or the like may be used instead of the numbers "1", "2", "3", . . . .

In the above-described embodiment, the target object on which the wearable device (belt main body) is mounted was a wrist of a body, but there is no limitation to this. The target object may be a site such as an arm, a torso, or a leg, or it may be a structure other than a body, or the like.

Also, the device 80 was mounted on the belt main body 10 in order to form a wearable device, but there is no limitation to this. The belt main body 10 may be configured alone as a belt.

Also, the device 80 was installed integrally in the belt main body 10, but there is no limitation to this. The device 80 and first belt portion 11, and the device 80 and second belt portion 12 may be coupled rotatably, for example, via known coupling rods (spring rods, or the like).

Also, the belt main body 10 was composed of a plastic material, but there is no limitation to this. The belt main body 10 may be formed using another material, such as a rubber material or a leather material.

The above-described embodiments are merely examples, and can be changed in various ways without departing from the scope of the invention. The above-described embodiments can be achieved separately, but it is also possible to combine embodiments. Also, the various characteristics in the different embodiments can be achieved separately, but it is also possible to combine characteristics in different embodiments.

REFERENCE SIGNS LIST 1, 501 Wearable device
10 Belt main body
11 First belt portion
12 Second belt portion
13, 113, 213, 513 Ring
14, 14A, 114, 214, 314, 414, 514, 714 Locking member
71, 72 Pressure sensor 150, 250 Removal mechanism
516 Fixing member

The invention claimed is:

1. A belt to be mounted by being wrapped around a substantially rod-shaped target object, comprising:
  a belt main body that is flexible and extends in the form of a long, narrow band;
  a frame-shaped body attached to a first belt portion that corresponds to a side on an end in a lengthwise direction of the belt main body;
  a plurality of through-holes formed in alignment in the lengthwise direction in a second belt portion corresponding to a side opposite to the first belt portion in the lengthwise direction of the belt main body; and
  a locking member configured separately from the belt main body, the locking member being attached to the second belt portion in a mode in which only a head portion of the locking member protrudes from a front surface of the second belt portion due to the head portion being pushed through a through-hole from a rear surface side of the second belt portion in advance, before the belt is mounted on the target object,
  wherein the locking member includes a flat base portion to be arranged in contact with the rear surface of the second belt, a neck portion that is continuous with the base portion and is to extend through the through-hole to the front surface of the second belt portion, and the head portion that is provided on a leading end of the neck portion and has a dimension greater than a dimension of the through-hole, and the locking member is formed integrally, and
  wherein in a state in which the belt main body is mounted on a target object, the second belt portion is passed through the frame-shaped body, and a side of the frame-shaped body locks the head portion of the locking member so as to prevent the second belt portion from coming out of the frame-shaped body.

2. The belt according to claim 1, wherein
  the head portion of the locking member attached to the through-hole of the second belt portion has, on a side near a leading end of the second belt portion in the lengthwise direction, an inclined surface that is inclined in an orientation of being located gradually farther away from the front surface of the second belt portion the farther from the leading end of the second belt portion it is.

3. The belt according to claim 2, wherein
  the shape of the through-hole of the second belt portion has a property in which, when rotated 180 degrees about an axis that passes through the center of the through-hole and is perpendicular to the second belt portion, the shape matches the original shape of the through-hole before rotation, and
  the shapes of the neck portion and the head portion of the locking member have a property in which, when rotated 180 degrees about the axis, the shapes match the original shapes of the neck portion and the head portion before rotation.

4. The belt according to claim 1, wherein
  in the head portion of the locking member attached to the through-hole of the second belt portion, a side surface on a side that is far from the leading end of the second belt portion in the lengthwise direction hangs over the opposing front surface of the second belt portion.

5. The belt according to claim 1, wherein
  the shape of the through-hole of the second belt portion has a property in which, when rotated 180 degrees about an axis that passes through the center of the through-hole and is perpendicular to the second belt portion, the shape is different from the original shape of the through-hole before rotation, and
  the shape of the neck portion of the locking member is substantially the same as the shape of the through-hole.

6. The belt according to claim 1, wherein
  at each position of the through-holes aligned in the lengthwise direction, the rear surface of the second belt portion has a recessed portion for determining a direction of the locking member about an axis that passes through the center of the through-hole and is perpendicular to the second belt portion, and
  the base portion of the locking member has a protrusion configured to fit into the recessed portion of the second belt portion only when the locking member is oriented in a specific direction about the axis.

7. The belt according to claim 1, wherein
  the base portion of the locking member attached to the through-hole of the second belt portion exists only in a region corresponding to the leading end side of the second belt portion from the neck portion in the lengthwise direction.

8. The belt according to claim 1, comprising
  a removal mechanism configured to, in a state in which the belt main body is mounted on the target object, release the locking member locked using the side of the frame-shaped body.

9. The belt according to claim 1, comprising
  a fixing member configured to, in a state in which the belt main body is mounted on the target object, fix a portion of the second portion that is past the side of the frame-shaped body to a corresponding portion of the first belt portion.

10. The belt according to claim 1, wherein
  a detection unit configured to detect tensile force of the belt main body is installed.

11. A wearable device comprising:
  the belt according to claim 1; and
  a device to be mounted on a body using the belt.

12. A belt to be mounted by being wrapped around a substantially rod-shaped target object, comprising:
  a belt main body that extends in the form of a long, narrow band;
  a frame-shaped body attached to a first belt portion that corresponds to a side on an end in a lengthwise direction of the belt main body;
  a plurality of through-holes formed in alignment in the lengthwise direction in a second belt portion corresponding to a side opposite to the first belt portion in the lengthwise direction of the belt main body; and
  a locking member that is configured separately from the belt main body and is configured to be attached to a through-hole of the second belt portion so as to protrude from a front surface of the second belt portion in advance, before the belt is mounted on the target object,
  wherein the locking member includes a base portion to be arranged in contact with the rear surface of the second belt, a neck portion that is continuous with the base portion and is to extend through the through-hole to the front surface of the second belt portion, and a head portion that is provided on a leading end of the neck portion and has a dimension greater than a dimension of the through-hole,
  in a state in which the belt main body is mounted on a target object, the second belt portion is passed through the frame-shaped body, and a side of the frame-shaped body locks the head portion of the locking member so as to prevent the second belt portion from coming out of the frame-shaped body, the shape of the through-hole of the second belt portion has a property in which, when rotated 180 degrees about an axis that passes through the center of the through-hole and is perpendicular to the second belt portion, the shape differs from the original shape of the through-hole before rotation, and the shape of the neck portion of the locking member is substantially the same as the shape of the through-hole, and thus the locking member is allowed to be attached in an original orientation in which the shape of the neck portion matches the shape of the through-hole, while the locking member is not allowed to be attached in a wrong orientation of being rotated 180 degrees about the axis.

13. A belt to be mounted by being wrapped around a substantially rod-shaped target object, comprising:

a belt main body that extends in the form of a long, narrow band;

a frame-shaped body attached to a first belt portion that corresponds to a side on an end in a lengthwise direction of the belt main body;

a plurality of through-holes formed in alignment in the lengthwise direction in a second belt portion corresponding to a side opposite to the first belt portion in the lengthwise direction of the belt main body; and a locking member that is configured separately from the belt main body and is configured to be attached to a through-hole of the second belt portion so as to protrude from a front surface of the second belt portion in advance, before the belt is mounted on the target object, wherein the locking member includes a base portion to be arranged in contact with the rear surface of the second belt, a neck portion that is continuous with the base portion and is to extend through the through hole to the front surface of the second belt portion, and a head portion that is provided on a leading end of the neck portion and has a dimension greater than a dimension of the through hole, in a state in which the belt main body is mounted on a target object, the second belt portion is passed through the frame-shaped body, and a side of the frame-shaped body locks the head portion of the locking member so as to prevent the second belt portion from coming out of the frame-shaped body, at each position of the through-holes aligned in the lengthwise direction, the rear surface of the second belt portion has a recessed portion for determining a direction of the locking member about an axis that passes through the center of the through-hole and is perpendicular to the second belt portion, and the base portion of the locking member has a protrusion that fits into the recessed portion of the second belt portion only when the locking member is oriented in a specific direction about the axis.

14. A belt to be mounted by being wrapped around a substantially rod-shaped target object, comprising:

a belt main body that extends in the form of a long, narrow band;

a frame-shaped body attached to a first belt portion that corresponds to a side on an end in a lengthwise direction of the belt main body;

a plurality of through-holes formed in alignment in the lengthwise direction in a second belt portion corresponding to a side opposite to the first belt portion in the lengthwise direction of the belt main body; and a locking member that is configured separately from the belt main body and is configured to be attached to a through-hole of the second belt portion so as to protrude from a front surface of the second belt portion in advance, before the belt is mounted on the target object, wherein the locking member includes a base portion to be arranged in contact with the rear surface of the second belt, a neck portion that is continuous with the base portion and is to extend through the through-hole to the front surface of the second belt portion, and a head portion that is provided on a leading end of the neck portion and has a dimension greater than a dimension of the through-hole, in a state in which the belt main body is mounted on a target object, the second belt portion is passed through the frame-shaped body, and a side of the frame-shaped body locks the head portion of the locking member so as to prevent the second belt portion from coming off of the frame-shaped body, and the base portion of the locking member attached to the through-hole of the second belt portion exists only in a region corresponding to the leading end side of the second belt portion from the neck portion in the lengthwise direction, which prevents a surface of the target object from being caught between the second belt portion and the base portion of the locking member when a portion of the second belt portion that is passed through the frame-shaped body and to which the locking member is attached is wrapped around the side of the frame-shaped body and bent in a process in which the belt is mounted on the target object.

* * * * *